US010235643B2

(12) United States Patent
Sawka

(10) Patent No.: US 10,235,643 B2
(45) Date of Patent: Mar. 19, 2019

(54) CLINICAL PLUG-IN APPLICATION

(75) Inventor: Matthew Nicholas Sawka, Smithville, MO (US)

(73) Assignee: Cerner Innovation, Inc., Kansas City, KS (US)

(*) Notice: Subject to any disclaimer, the term of this patent is extended or adjusted under 35 U.S.C. 154(b) by 790 days.

(21) Appl. No.: 13/248,680

(22) Filed: Sep. 29, 2011

(65) Prior Publication Data
US 2013/0085764 A1    Apr. 4, 2013

(51) Int. Cl.
| G06Q 10/06 | (2012.01) |
| G06Q 50/22 | (2018.01) |
| G06F 19/00 | (2018.01) |
| G16H 40/40 | (2018.01) |

(52) U.S. Cl.
CPC .......... G06Q 10/06 (2013.01); G06F 19/00 (2013.01); G06Q 50/22 (2013.01); G16H 40/40 (2018.01)

(58) Field of Classification Search
CPC ............... G06Q 50/22; G06Q 50/24; G06F 19/322–19/327
USPC ........................................ 705/2, 3
See application file for complete search history.

(56) References Cited

U.S. PATENT DOCUMENTS

| 6,324,648 | B1 | 11/2001 | Grantges, Jr. |
| 7,436,311 | B2 | 10/2008 | Rapaport et al. |
| 7,520,419 | B2 | 4/2009 | Libin et al. |
| 7,907,966 | B1 | 3/2011 | Mammen |
| 8,321,566 | B2 | 11/2012 | Schroeder et al. |
| 8,583,728 | B2 | 11/2013 | Irwin et al. |
| 2002/0010679 | A1* | 1/2002 | Felsher ................. G06F 19/328 705/51 |
| 2002/0032583 | A1* | 3/2002 | Joao ..................... G06F 19/328 705/2 |
| 2002/0184054 | A1 | 12/2002 | Cox et al. |
| 2005/0228808 | A1 | 10/2005 | Mamou et al. |
| 2006/0077941 | A1 | 4/2006 | Alagappan et al. |
| 2006/0161457 | A1* | 7/2006 | Rapaport ............... G06Q 10/10 705/2 |
| 2006/0230286 | A1 | 10/2006 | Kitada |
| 2007/0203753 | A1 | 8/2007 | Hasan et al. |
| 2008/0306872 | A1 | 8/2008 | Felsher |
| 2009/0076855 | A1 | 3/2009 | McCord |
| 2009/0164252 | A1 | 6/2009 | Morris et al. |

(Continued)

OTHER PUBLICATIONS

First Action Interview Office Action in U.S. Appl. No. 13/248,662 dated Jun. 11, 2013, 13 pages.

(Continued)

*Primary Examiner* — Minnah L Seoh
*Assistant Examiner* — Joshua B Blanchette
(74) *Attorney, Agent, or Firm* — Shook, Hardy and Bacon LLP

(57) ABSTRACT

Methods, computer systems, and computer-storage media for accessing clinical information on a mobile device are provided. A plug-in application receives from a mobile device a set of authorization credentials and a request for clinical information. A set of clinical information is determined based on the set of authorization credentials. The set of clinical information is retrieved from clinical information servers, and the set of clinical information is parsed and populated into a generic hierarchical structure. The populated hierarchical structure is communicated to the mobile device where it is subsequently rendered for display.

13 Claims, 16 Drawing Sheets

(56) References Cited

U.S. PATENT DOCUMENTS

| | | | |
|---|---|---|---|
| 2009/0259493 | A1 | 10/2009 | Venon et al. |
| 2010/0082372 | A1 | 4/2010 | Wen et al. |
| 2010/0217618 | A1 | 8/2010 | Piccirillo et al. |
| 2010/0292556 | A1 | 11/2010 | Golden |
| 2011/0119076 | A1 | 5/2011 | Dhoble |
| 2011/0246565 | A1* | 10/2011 | Irwin .................. H04L 67/02 709/203 |
| 2012/0232929 | A1 | 11/2012 | Experton |
| 2012/0323606 | A1 | 12/2012 | Ananthasubramaniam et al. |
| 2013/0085776 | A1 | 4/2013 | Sawka |

OTHER PUBLICATIONS

Preinterview First Action Interview in U.S. Appl. No. 13/248,662 dated Mar. 12, 2013, 11 pages.

Final Office Action in U.S. Appl. No. 13/248,662 dated Oct. 22, 2012, 34 pages.

Final Office Action dated Feb. 10, 2016 in U.S. Appl. No. 13/248,662, 9 pages.

Non-Final Office Action dated May 6, 2016 in U.S. Appl. No. 13/248,662, 23 pages.

Final Office Action dated Jun. 29, 2015 in U.S. Appl. No. 13/248,662, 10 pages.

Non-Final Office Action dated Nov. 20, 2014 in U.S. Appl. No. 13/248,662, 19 pages.

Non-Final Office Action dated Oct. 22, 2015 in U.S. Appl. No. 13/248,662, 7 pages.

Final Office Action dated Nov. 17, 2016 in U.S. Appl. No. 13/248,662, 11 pages.

Notice of Allowance dated Sep. 8, 2017 in U.S. Appl. No. 13/248,662, 8 pages.

Non-Final Office Action received for U.S. Appl. No. 13/248,662, dated May 1, 2017, 10 pages.

* cited by examiner

US 10,235,643 B2

CLINICAL PLUG-IN APPLICATION

CROSS-REFERENCE TO RELATED APPLICATIONS

This application is related by subject matter to U.S. patent application Ser. No. 13/248,662 entitled "Clinical Framework Application For Mobile Devices," which is assigned or under obligation of assignment to the same entity as this application. U.S. patent application Ser. No. 13/248,662 is expressly incorporated by reference herein. The two applications are being filed on the same date.

BACKGROUND

Traditionally, clinicians have only been able to access sensitive healthcare information regarding their patients while physically located at a healthcare facility. Further, this healthcare information is often delivered via secured wired systems. Although healthcare applications exist for mobile platforms, the applications typically do not allow access to sensitive healthcare information outside of the four walls of the healthcare facility. As well, because of the diversity of operating platforms that exist for mobile devices, solution teams face a daunting challenge crafting healthcare applications in a timely manner that are adapted to these diverse platforms.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, a clinical plug-in application that can be used with a variety of mobile device operating platforms. The plug-in application interacts with a framework application on a mobile device to receive requests for clinical information, retrieve the clinical information, and deliver the information to the mobile device. Because the plug-in application works with a variety of mobile device operating platforms, solution teams can quickly build plug-in applications that address a variety of healthcare-related concerns without worrying about crafting applications for each different operating system.

BRIEF DESCRIPTION OF THE DRAWINGS

Embodiments are described in detail below with reference to the attached drawing figures, wherein.

DETAILED DESCRIPTION

Figure 1:
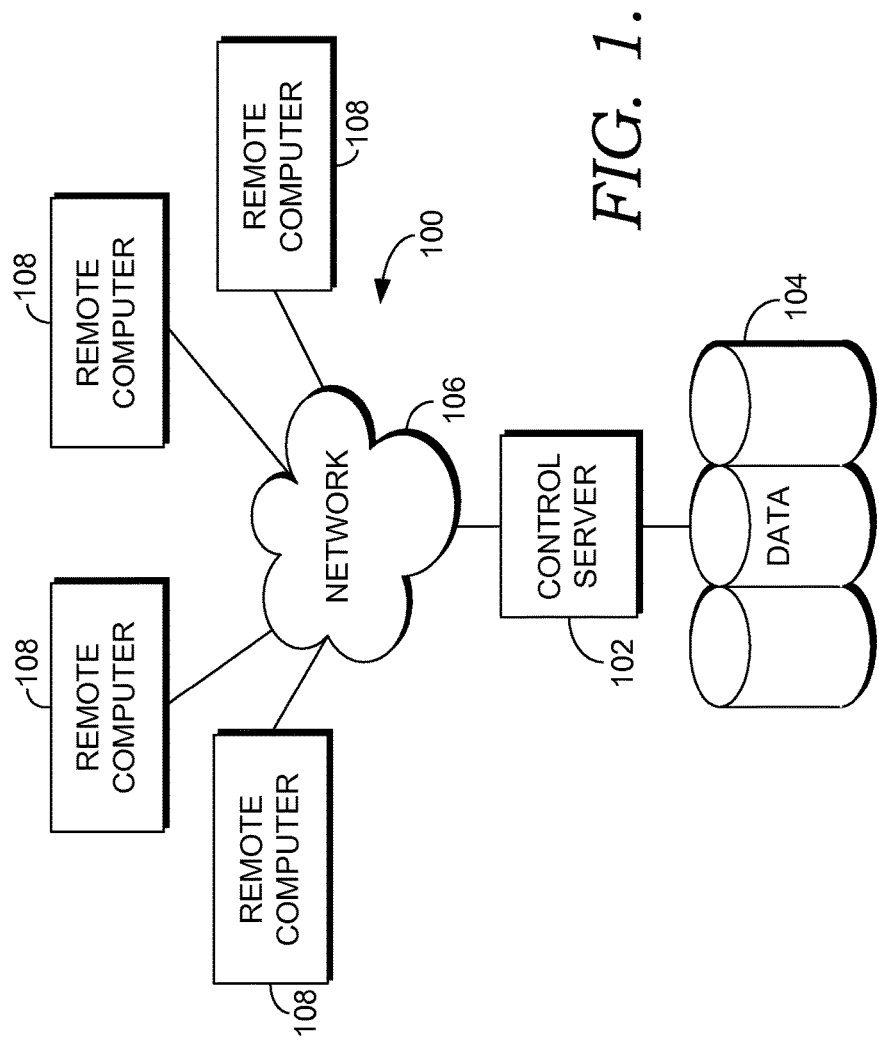
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, computer systems, and computer storage media for use in enabling a clinician to access and view clinical information on a mobile device, as well as enabling the clinician to place a clinical order on the mobile device using native controls. In one aspect, a framework application on a mobile device receives a request for clinical information from a user. After authenticating the user, the mobile device determines a number of plug-in applications that are associated with the user. After the request for clinical information is communicated to the plug-in applications, clinical information is received from the plug-in applications. This clinical information is subsequently displayed on the mobile device.

In another aspect, a clinician is able to utilize the native controls present on the mobile device to place a clinical order outside of a traditional healthcare facility. With respect to this aspect, the mobile device receives a request for clinical information from a user. After the user is authenticated, one or more plug-in applications are determined for the user. The request for clinical information is communicated to the plug-in applications. The plug-in applications return the clinical information to the mobile device; the clinical information includes an action item in the form of a uniform resource locator (URL) with a set of placeholders. Utilizing the native controls on the mobile device, the user inputs a one or more values. The set of placeholders are replaced with these values, and, subsequently, the URL is communicated to the plug-in applications.

In yet another aspect, a plug-in application on a mobile device interacts with a framework application on the mobile device to retrieve clinical information which is then presented to a user of the mobile device. The plug-in application receives from the mobile device a request for clinical information as well as a set of authorization credentials. Using the authorization credentials, the plug-in application determines a set of clinical information associated with the user of the mobile device and retrieves the set of clinical information. The clinical information is populated into a generic hierarchical structure and communicated to the mobile device where it is subsequently rendered for display.

In an additional aspect, a plug-in application interacts with a framework application on a mobile device to enable a clinician to place a clinical order outside of a healthcare facility. The plug-in application receives from the mobile device a set of authorization credentials associated with the clinician as well as a request for clinical information. The clinical information is retrieved. The plug-in application then determines that an action item is associated with one of the items of clinical information; the action item includes an action item URL with a set of placeholders. The clinical information, including the action item, is populated into a generic hierarchical structure and communicated to the mobile device. The plug-in application then receives the URL from the mobile device; the URL placeholders have been replaced with a set of user-inputted values. The user-inputted values are extracted, a clinical order is created, and the clinical order is communicated to an order server.

Having briefly described embodiments of the present invention, an exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

A. Clinical Application Framework for Mobile Devices

In one embodiment, the present invention enables a clinician to access clinical information, including clinical patient information, outside of a healthcare facility. A framework application, which is built on an operating system of the mobile device, interacts with one or more plug-in applications to access the clinical information which is subsequently rendered for display to the clinician. As well, the framework application enables the clinician to use the native controls of the mobile device in combination with the plug-in applications to create a clinical order.

Figure 2:
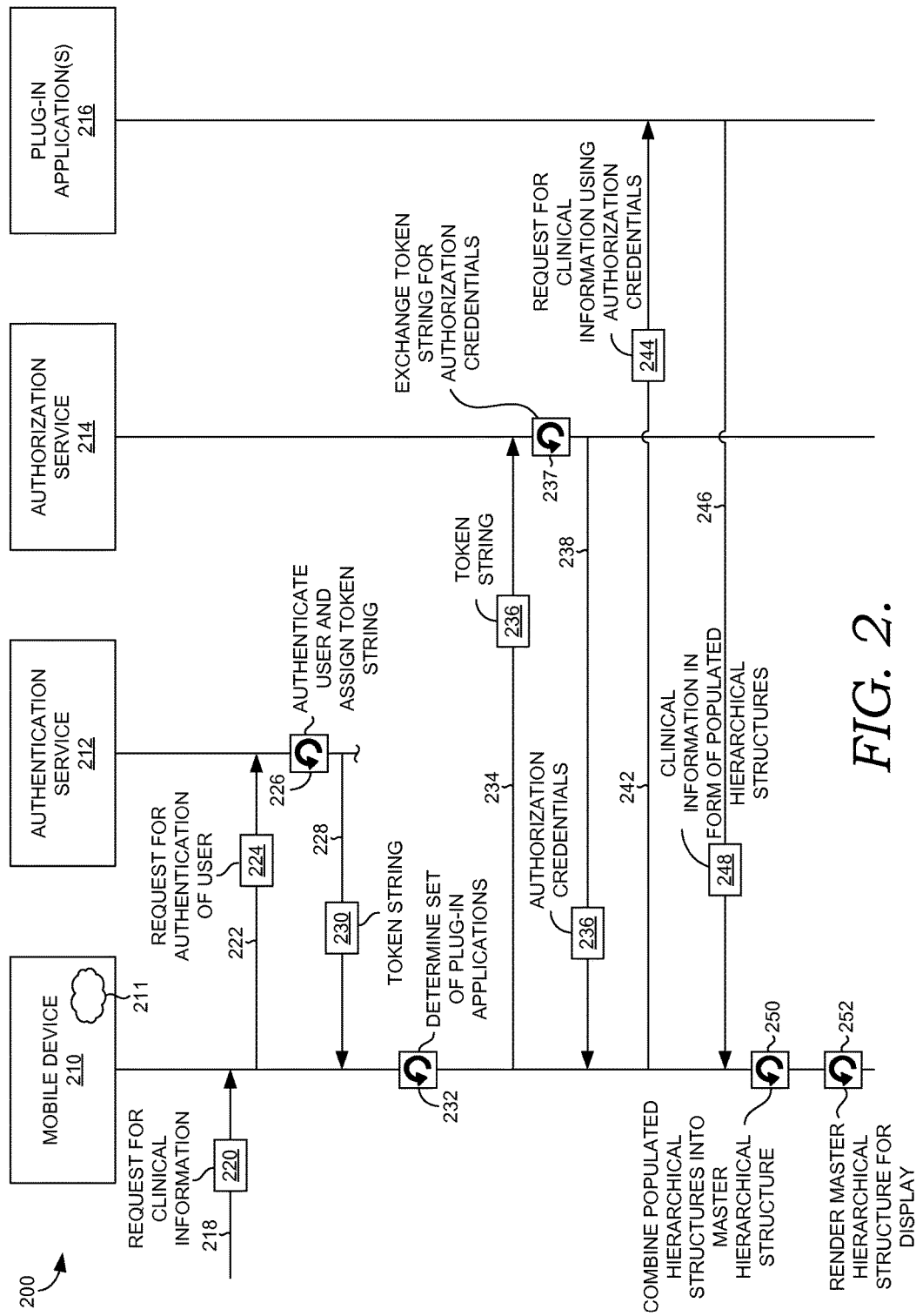
FIG. 2 depicts an illustrative process-flow diagram that depicts a method of receiving and rendering clinical information on a mobile device according to an embodiment of the present invention.

Turning now to FIG. 2, a process-flow diagram, referenced generally by the numeral 200, is depicted illustrating a method of receiving and rendering clinical information on a mobile device. FIG. 2 includes a mobile device 210, an authentication service 212, an authorization service 214, and one or more plug-in applications 216.

The mobile device 210 may be any type of wireless-telecommunications device. Such devices may include fixed, mobile, and portable devices including cellular telephones, personal digital assistants, tablet personal computers (tablet PCs), and devices that are built into automobiles, televisions, computers, and the like. The mobile device 210 may include global positioning system (GPS) technology. Further, the mobile device 210 includes a set of native controls. These native controls are well-known in the art and may include drop-down lists, spinners, free text, slide bars, flicks, pinch and stretch, drag, and the like.

The mobile device 210 has a framework application 211 that enables the mobile device 210 to receive and render clinical information. The framework application 211 also enables a user of the mobile device 210 to place a clinical order using native controls. The framework application 211 is native to the operating system of the mobile device 210.

The authentication service 212 is associated with a healthcare facility to which the user is affiliated. The authentication service 212 authenticates the user and may only be accessed through a client gateway; this process will be explained in greater depth below. Like the authentication service 212, the authorization service 214 is associated with the healthcare facility to which the user if affiliated. The authorization service 214 may, in one aspect, comprise a data store that stores any number of authorization credentials for any number of users.

The plug-in application 216 comprises a solution-specific application that interacts with the framework application 211 through an application programming interface (API). The API allows third-party solution teams to quickly build a variety of plug-in applications 216 that can interact with a number of different framework applications 211 residing on different types of mobile devices 210 in order to access and retrieve a variety of clinical information. In other words, the third-party solution teams are not required to build separate applications for each operating system of the different types of mobile devices 210. Each plug-in application 216 may be able to access and retrieve a different set of clinical information.

Continuing with respect to FIG. 2, at step 218, a request 220 for clinical information is received from the user of the mobile device 210. The request 220 may include, for example, requests for: a list of clinical patients that are associated with the user, clinical patients that are located close to the user, intravenous (IV) pump locations that are located close to the user, clinical patient information (for example, requests for lab results, procedure results, clinical orders, vital signs, etc.), scheduling and staffing information associated with one or more clinicians at the healthcare facility, clinical ordering information, and the like.

Figure 4:
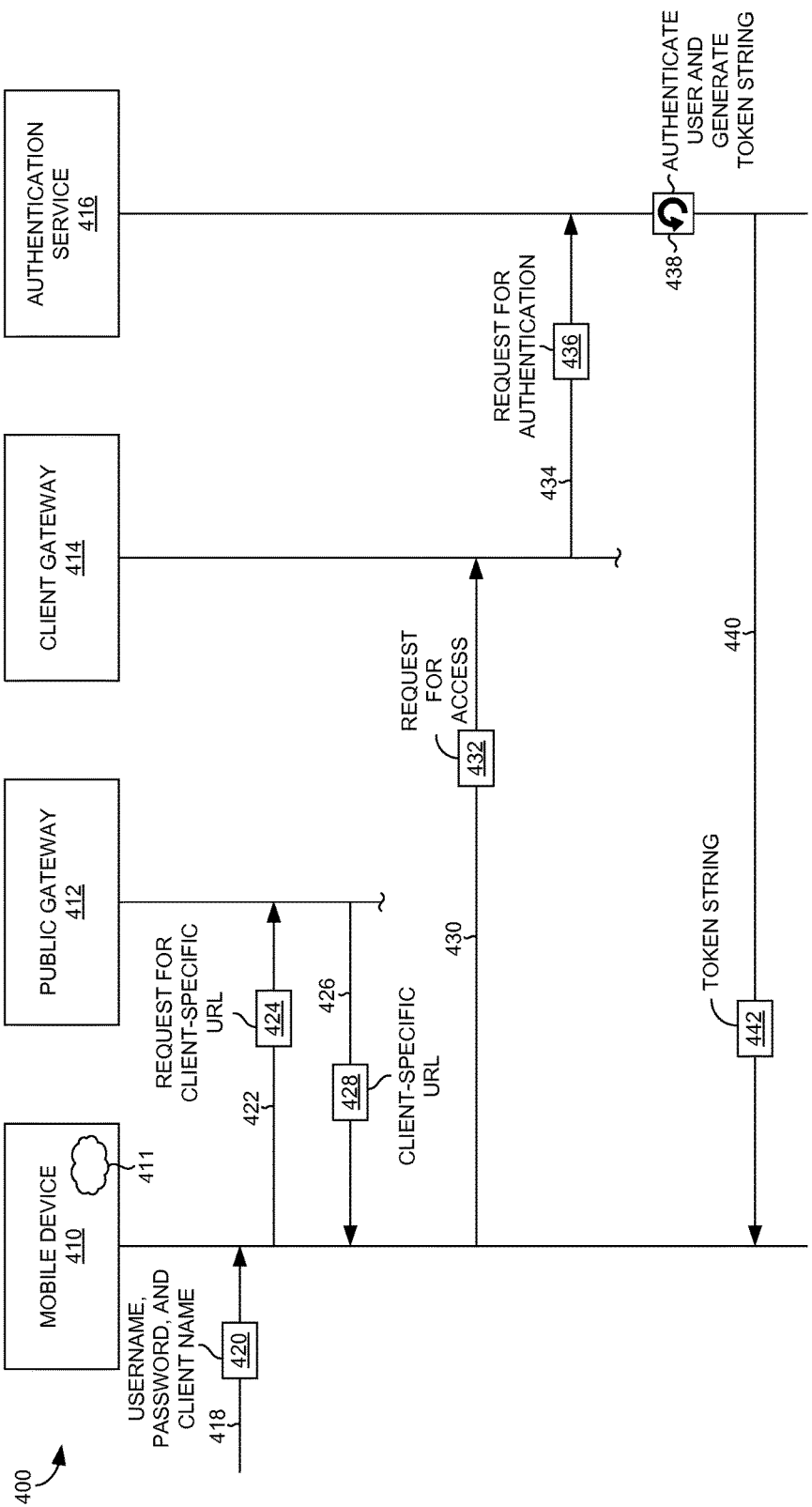
FIG. 4 depicts an illustrative process-flow diagram that depicts a method of authenticating a user of a mobile device according to an embodiment of the present invention.

At step 222, the mobile device 210 communicates a request 224 for authentication of the user to the authentication service 212. This process is detailed in FIG. 4. FIG. 4 depicts a process-flow diagram, referenced generally by the numeral 400, illustrating a method of authenticating a user. FIG. 4 includes a mobile device 410 with a framework application 411, a public gateway 412, a client gateway 414, and an authentication service 416. The mobile device 410, the framework application 411, and the authentication service 416 may be, for example, the mobile device 210, the framework application 211, and the authentication service 212 of FIG. 2.

The public gateway 412 is accessible to any user. Further, the user does not have to be located at a healthcare facility to access the public gateway 412. In one aspect, the public gateway 412 is associated with a third party that creates and markets the plug-in applications. The client gateway 414 is associated with a specific healthcare facility (hereinafter known as a "client"). At step 418, the mobile device 410 receives a username, password, and a client name 420 from the user. For example, the user may be presented with a log-in screen on the mobile device 410 after making the request for clinical information. The log-in screen allows the user to input the username, password, and the client name 420.

At step 422, the mobile device 410 communicates a request 424 for a client-specific URL to the public gateway 412. The client-specific URL is a URL that directs the user to the client gateway 414. At step 426, the mobile device 410 receives the client-specific URL 428 from the public gateway 412. Using the client-specific URL 428, at step 430, the mobile device 410 makes a request 432 for access to the client gateway 414. After granting access, at step 434, the client gateway 414 makes a request 436 for authentication of the user from the authentication service 416.

At step 438, the authentication service 416 verifies that the user is associated or affiliated with the client and assigns a token string to the user. The token string may be a combination of alphanumeric characters and is a secure way to identify the user by indicating that the user is securely logged in and authenticated. The token string may not only represent the user, but may also represent a user role. Examples of a user role include physician, nurse, respiratory therapist, and the like. At step 440, the token string 442 is communicated to the mobile device 410.

Turning back to FIG. 2, at step 226, the authentication service 212 authenticates the user and assigns the user a token string as outlined above. At step 228, the token string 230 is received by the mobile device 210. At step 232, the mobile device 210 determines a set of plug-in applications 216 associated with the user based on the token string 230. As mentioned above, different plug-in applications 216 are used to access and retrieve different sets of clinical information. As well, different users or user roles (as represented by the token string 230) will have access to different sets of clinical information. For example, a respiratory therapist would likely not have access to nurse scheduling information. Likewise, sensitive patient information may only be accessed by certain clinicians. Thus, the mobile device 210 uses the token string 230 to determine what type of clinical information is available to the user or user role associated with the token string 230.

At step 234, a token string 236 is communicated to the authorization service 214. The token string 236 comprises the token string 230 along with additional information such as the set of plug-in applications 216 that have been determined for the user. At step 237, a determination is made as to what set of authorization credentials are associated with the token string 236, and the token string 236 is exchanged for the set of authorization credentials. The token string 236 may be associated with more than one set of authorization credentials. For example, the token string 236 may represent an individual nurse and a nursing role such as a nurse shift manager. Thus, one set of authorization credentials may be associated with the individual nurse; this set of authorization credentials will enable access to clinical information important to the individual nurse such as a patient list. As well, another set of authorization credentials may be associated with the nursing role. This set of authorization credentials will enable access to clinical information such as nurse staffing information. On the other hand, a determination may be made at step 237 that the token string 236 is not associated with a set of authorization credentials. If this is the case, a message may be delivered to the mobile device 210 informing the user that access to the clinical information has been denied. At step 238, the set of authorization credentials 240 are received by the mobile device 210.

At step 242, a request 244 is communicated to the plug-in application(s) 216 for clinical information. The request 244 is communicated along with the set of authorization credentials 240. The set of authorization credentials 240 are used by the plug-in application(s) 216 to retrieve the requested clinical information. This aspect will be explored in greater depth below.

At step 246, the clinical information 248 is received by the mobile device 210. The clinical information 248 is received in the form of one or more populated generic hierarchical structures (i.e., the clinical information 248 is populated into a generic hierarchical structure). In one aspect, each plug-in application 216 delivers a different populated hierarchical structure containing a different type of clinical information 248. For example, a first plug-in application 216 may return clinical information 248 related to IV pump locations. This clinical information 248 is received in the form of a first populated hierarchical structure. Likewise, a second plug-in application 216 may return clinical information 248 related to a patient list. This clinical information 248 is received in the form of a second populated hierarchical structure, and so on.

At step 250, the populated hierarchical structures are combined by the mobile device 210 into a master hierarchical structure. The master hierarchical structure contains all of the received clinical information 248 from the plug-in application(s) 216. At step 252, the master hierarchical structure is rendered for display on the mobile device 210.

The clinical information 248 received at step 246 may include items of the clinical information 248 (clinical items) such as patients on a patient list. Additionally, the clinical information 248 may specify that a clinical item is associated with one or more URLs directed to one or more Web pages. These Web pages may be static (a Web page that is delivered to the user exactly as stored), or dynamic (a Web page generated by a Web application). By way of illustrative example, the clinical information 248 may include a list of patients. The patient list is displayed on the mobile device 210 to the user. When the user selects a patient on the patient list, the user is presented with a dynamic Web page that provides up-to-date patient information. As well, the clinical information 248 may also include rendering instructions used by the mobile device 210 to render the populated hierarchical structure for display to the user. For example, the rendering instructions may specify that the items of the clinical information 248 should be displayed as a list-type view.

Alternatively, in another aspect of the invention, the clinical information 248 may be in the form of one or more URLs associated with hypertext markup language (HTML) Web pages. Thus, instead of displaying the clinical information 248 as a series of clinical items, the clinical information 248 is displayed as one or more HTML Web pages. In both of these cases (i.e., clinical items with associated URLs, or HTML Web pages), a refresh rate may be specified, and the clinical item or the HTML Web page will be reloaded based on the specified rate.

Figure 3:
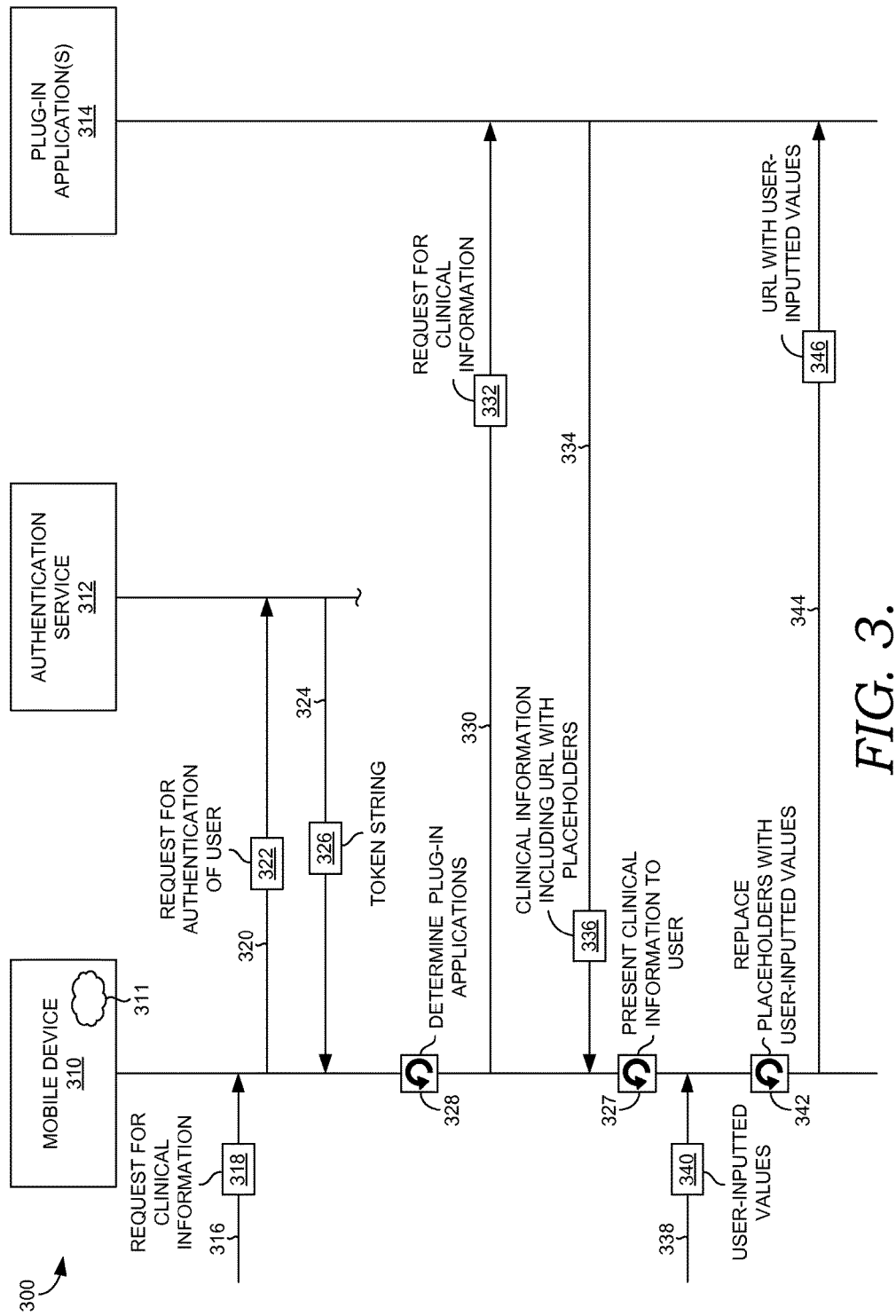
FIG. 3 depicts an illustrative process-flow diagram that depicts a method of creating a clinical order on a mobile device according to an embodiment of the present invention.

Turning now to FIG. 3, a process-flow diagram, referenced generally by the numeral 300, is depicted illustrating a method of creating a clinical order on a mobile device. FIG. 3 includes a mobile device 310 with a framework application 311, an authentication service 312, and one or more plug-in applications 314. The mobile device 310, the framework application 311, the authentication service 312, and the plug-in application(s) 314 may be the same as the mobile device 210, the framework application 211, the authentication service 212, and the plug-in application(s) 216 of FIG. 2. As well, many of the steps outlined in FIG. 3 correspond to the steps outlined in FIG. 2. As such, not as much detail will be included for these redundant steps.

At step 316, a request 318 for clinical information is received from a user of the mobile device 310. The request 318 includes a request to place a clinical order for one or more patients. At step 320, a request 322 for authentication of the user is communicated to the authentication service 312. At step 325, a token string 326 is received by the mobile device 310. The token string 326 identifies and authenticates the user or a user role. The token string 326 may correspond to the token string 230 of FIG. 2.

At step 328, the mobile device 310 determines a set of plug-in applications 314 using the token string 326. And, at step 330, a request 322 for clinical information is communicated to the plug-in application(s) 314. The request 322 may include the token string 326. Continuing, at step 334, clinical information 336 is received by the mobile device 310 from the plug-in application(s) 314.

The clinical information 336 includes at least one action item comprising an action item URL with a set of placeholders. The action item may also include rendering instructions for rendering a display on the mobile device 310. The display enables the user to input one or more values using the native controls of the mobile device 310. The action item is associated with an item of the clinical information 336. For instance, the item may be a patient name, and the action item may be associated with the patient name. By way of illustrative example, the action item URL may comprise the following URL: http:// . . . /orders/drugs=!&patient=!&dose=!&freq=!&unit=!&route=!&user=abc. The action item URL has a set of placeholders (the character "!") for the type of drug, the patient, the dose of the drug, the frequency of administration of the drug, the unit of measurement of the drug, and the route of administration of the drug. As well, the action item URL comprises a segment identifying the user (user=abc). This could by the token string 326 or a set of authorization credentials as outlined above with respect to FIG. 2. There are numerous examples of action item URLs associated with any number of potential clinical orders. Any and all such variations are within the scope of embodiments of the present invention.

At step 327, the clinical information 336 is presented to the user. For example, assuming the clinical information 336 comprises a patient list, the patient list is presented to the user on a display screen of the mobile device. When the user selects a patient from the patient list, a display screen is presented to the user that has one or more input fields for receiving user-inputted values.

At step 338, one or more user-inputted values 340 are received from the user. The framework application 311 on the mobile device 310 allows the user to input values using the native controls of the phone. For example, the action item may include data specifying generic actions that correspond to the native controls on the mobile device 310; this data is known as an action behavior type. For example, the action behavior type may specify that a certain user input is best suited for a drop-down list, while another user input is best suited for free text entry. The framework application 311 uses the action behavior type to determine a native control that corresponds to the action behavior type. The user utilizes the native controls of the mobile device 310 to input a set of values corresponding to the placeholders in the URL. By way of illustrative example using the exemplary URL recited above, the user could use free text to input a dose, a spinner control to input a frequency, a drop-down list to enter a unit, and so on.

At step 342, the mobile device 310 replaces the placeholders of the action item URL with the set of user-inputted values. Using the exemplary action item URL, the new action item URL may comprise: http:// . . . /orders/drugs=acet&patient=1256&dose=200&freq=QID&unit=mg&route=po&user=abc. At step 344, the new action item URL 346 is communicated to the plug-in application 314. The new action item URL 346 comprises the original action item URL with the user-inputted values. After receiving the action item URL 346 from the mobile device 310, the plug-in application 314 creates a clinical order and communicates the clinical order to an order server. This process will be explained in greater depth below.

Figure 5:
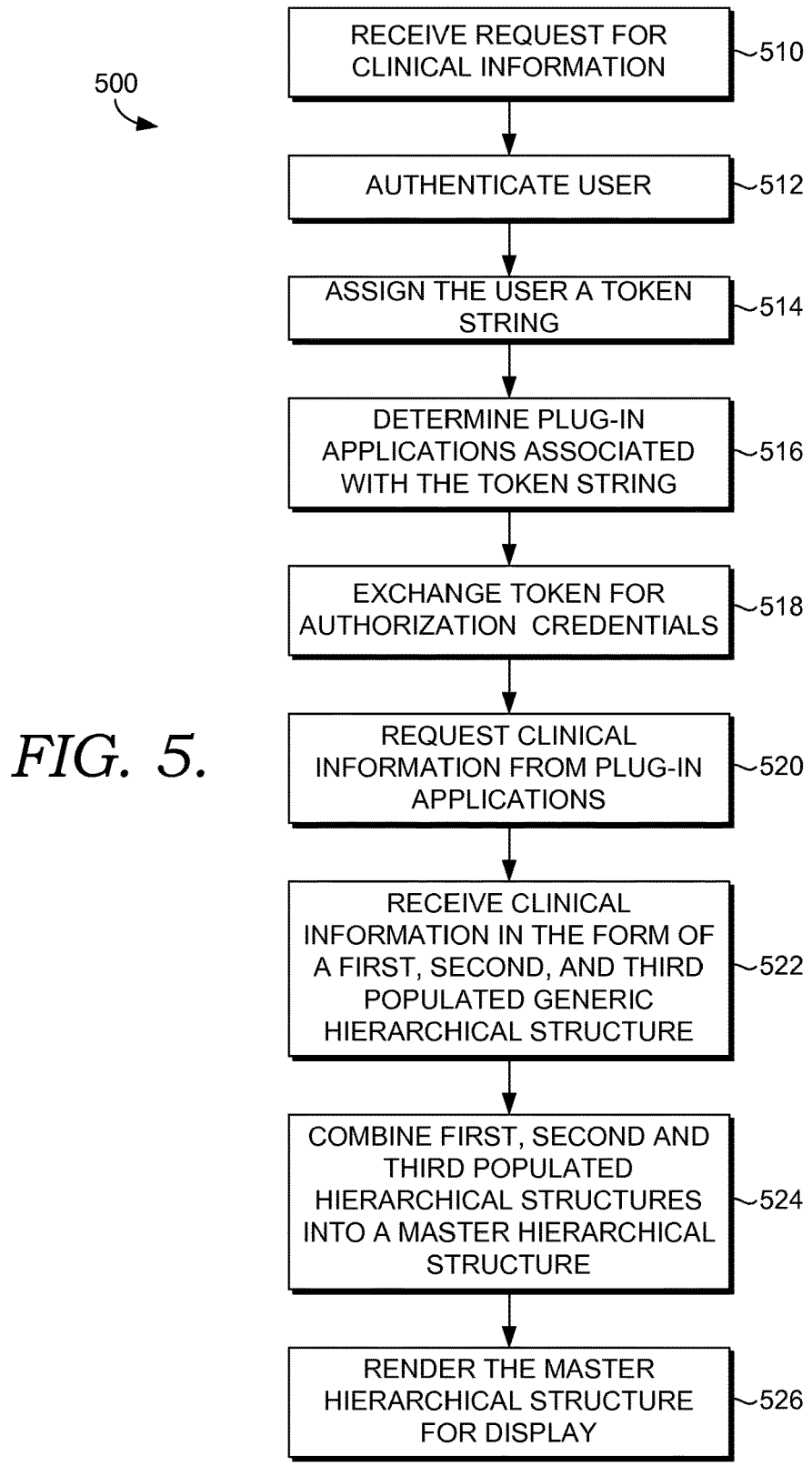
FIG. 5 depicts a flow diagram illustrating a method of receiving and rendering clinical information received from a plurality of plug-in applications on a mobile device according to an embodiment of the present invention.

Turning now to FIG. 5, a flow diagram illustrating a method of receiving and rendering clinical information on a mobile device is depicted and is referenced generally by the numeral 500. At step 510, a request for clinical information is received from a user. The user may be a clinician, and the request for clinical information may include clinical information related to one or more patients, or general clinical information such as equipment location and availability information, scheduling and staffing information, clinical ordering information, and the like.

At step 512, the user is authenticated by an authentication service such as the authentication service 416 of FIG. 4. The user may be authenticated by inputting, for example, a username, a password and some type of client identifier. Upon inputting this information and determining its validity, a public gateway provides a client-specific URL that is used to access a client gateway. The client gateway is associated with a healthcare facility of which the user is affiliated. The client gateway requests authentication of the user from the authentication service. Upon verifying the user's identity, the authentication service assigns a token string to the user at step 514. The token string may represent a user identity and/or a user role.

At step 516, a set of plug-in applications associated with the user is determined. The set of plug-in applications may be determined using the token string assigned by the authentication service. As mentioned, the token string represents a user identity or a user role. Based on user identity, a first set of plug-in applications may be determined for the user, and based on user role, a second set of plug-in applications may be determined for the user.

After the set of plug-in applications have been determined, at step 518, the token string is exchanged for a set of authorization credentials from, for example, an authorization service such as the authorization service 214 of FIG. 2. The authorization service may comprise a data store of authorization credentials associated with any number of users or user roles. Once the authorization service receives the token string, it determines one or more sets of authorization credentials associated with the user or user role identified by the token string. The authorization credentials, in one aspect, act as a further level of security to prevent non-privileged users from accessing private healthcare information.

At step 520, a request for clinical information is communicated to the set of plug-in applications. The request may be made using the authorization credentials received from the authorization service in exchange for the token string. One set of authorization credentials may allow access to one set of plug-in applications, while a second set of authorization credentials may allow access to another set of plug-in applications.

At step 522, a set of clinical information is received from the plug-in applications. Each plug-in application returns a different set of clinical information in the form of a populated generic hierarchical structure. For example, a first plug-in application may return a first populated hierarchical structure, a second plug-in application may return a second populated hierarchical structure, and a third plug-in application may return a third populated hierarchical structure. Each set of clinical information includes not only the requested clinical information but also rendering instructions that is used by the mobile device to render the clinical information for display to the user. The rendering instructions may include data specifying a display format for the clinical information. Each set of clinical information may also include one or more URLs associated with clinical items within the set of clinical information. The URLs may correspond to static Web pages or dynamic Web pages. Upon selection of one of the clinical items, the user may be directed to a static Web page or a dynamic Web page that provides the user with additional information about the clinical item.

At step 524, the first, second, and third populated generic hierarchical structures are combined into a master hierarchical structure. The details regarding how the hierarchical structure is organized will be explained in greater depth below. The master hierarchical structure contains all of the requested clinical information along with rendering data needed to render the clinical information for display to the user.

At step 526, the master hierarchical structure is rendered for display on the mobile device. In one aspect, the clinical information contained within the master hierarchical structure is extracted from the master hierarchical structure along with rendering data. The rendering data is used by the mobile device to organize the clinical information into a user-friendly display. For example, the rendering data may specify that a static piece of text be displayed as is. Also, the rendering data may specify that if a certain item of clinical information contains several pieces of information, the pieces of information should be rendered according to a certain order.

Figure 6:
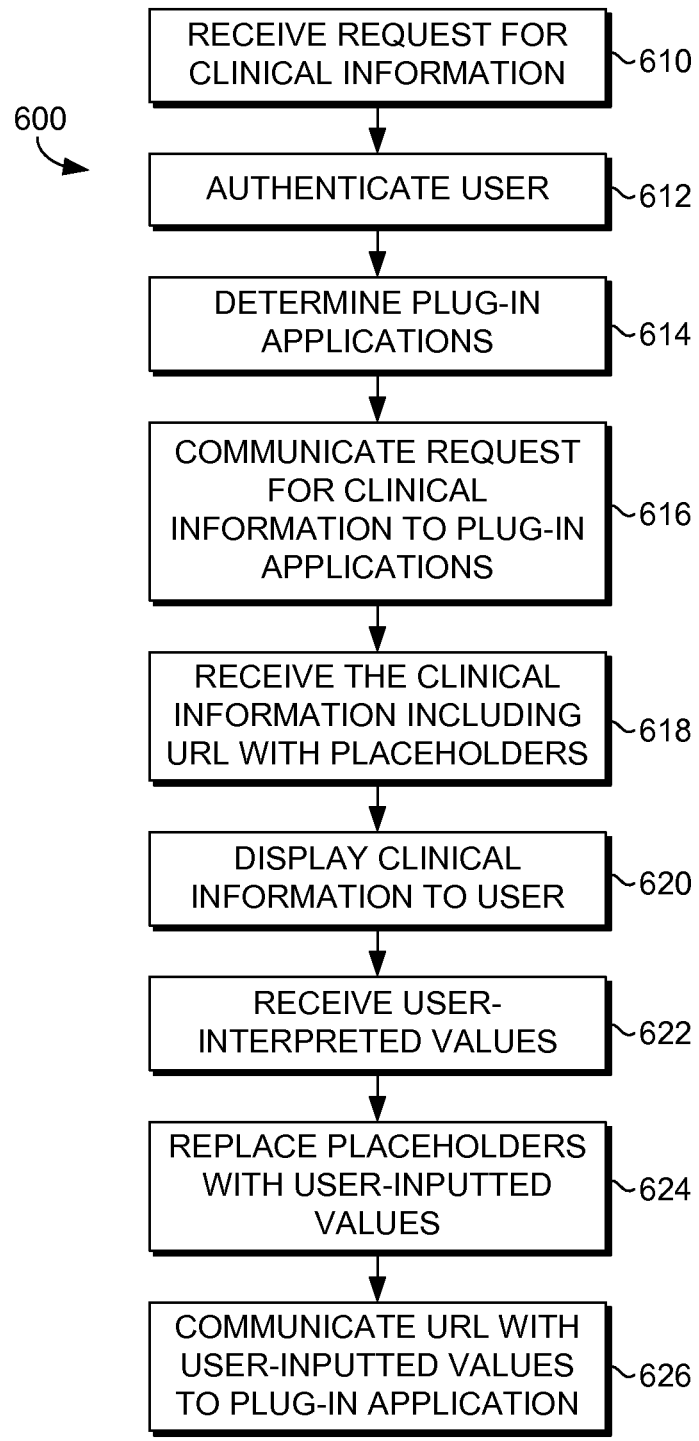
FIG. 6 depicts a flow diagram illustrating a method of creating a clinical order on a mobile device according to an embodiment of the present invention.

Turning now to FIG. 6, a flow diagram is depicted illustrating a method of creating a clinical order on a mobile device and is referenced generally by the numeral 600. At step 610, a request for clinical information is received from a user. For example, the user may request clinical information for a clinical patient, and additionally, the user may request to place a clinical order for the patient. At step 612, the user is authenticated as outlined above. At step 614, a set of plug-in applications is determined for the authenticated user, and, at step 616, a request for the clinical information is communicated to the set of plug-in applications.

At step 618, the clinical information is received from the plug-in applications. The clinical information includes one or more items of the clinical information associated with one or more action items. In turn, an action item comprises at least an action item URL with a set of placeholders. The action item URL is used to place a clinical order. The action item also includes other data including an action behavior type that specifies generic actions that generally correspond to native controls on the mobile device. The action item may also include rendering instructions that are used by the mobile device to render a display screen by which the user inputs values.

At step 620, the clinical information, including items of the clinical information, is displayed on the mobile device. When the user selects an item of the clinical information associated with an action item, the user is directed to a display screen that enables the user to input values using the native controls on the mobile device. By way of illustrative example, a user may select a patient name and be directed to a display screen that enables the user to place a clinical order for acetaminophen.

At step 622, a set of user-inputted values is received from the user. As mentioned above, the user is able to utilize the native controls of the user's mobile device to input the values. Different input fields may require the user to use different native controls. For example, an input field for the type of drug may require free text, while an input field for unit might require a drop-down list. Each action item may require a different set of inputs. Any and all variations are within the scope of the invention.

At step 624, the placeholders of the action item URL are replaced with the user-inputted values, and, at step 626, the action item URL with the user-inputted values is communicated to one or more of the plug-in applications. The plug-in application subsequently creates a clinical order utilizing the action item URL and the user-inputted values and communicates the clinical order to an order server. This will be explained in greater depth below.

In conclusion, a clinical framework application for a mobile device enables a user to access and view sensitive clinical information on the mobile device. This is accomplished by the framework application interacting with a set of plug-in applications that retrieve the clinical information and return it to the framework application, where it is subsequently rendered for display to the user. As well, the framework application enables the user to place a clinical order on the mobile device. The framework application receives a URL with a set of placeholders from a plug-in application. After receiving one or more user-inputted values, the framework application replaces the placeholders with the user-inputted values and returns the URL to the plug-in application. The plug-in application subsequently creates a clinical order utilizing the user-inputted values, and communicates the clinical order to an order server.

B. Clinical Plug-In Application

Figure 7:
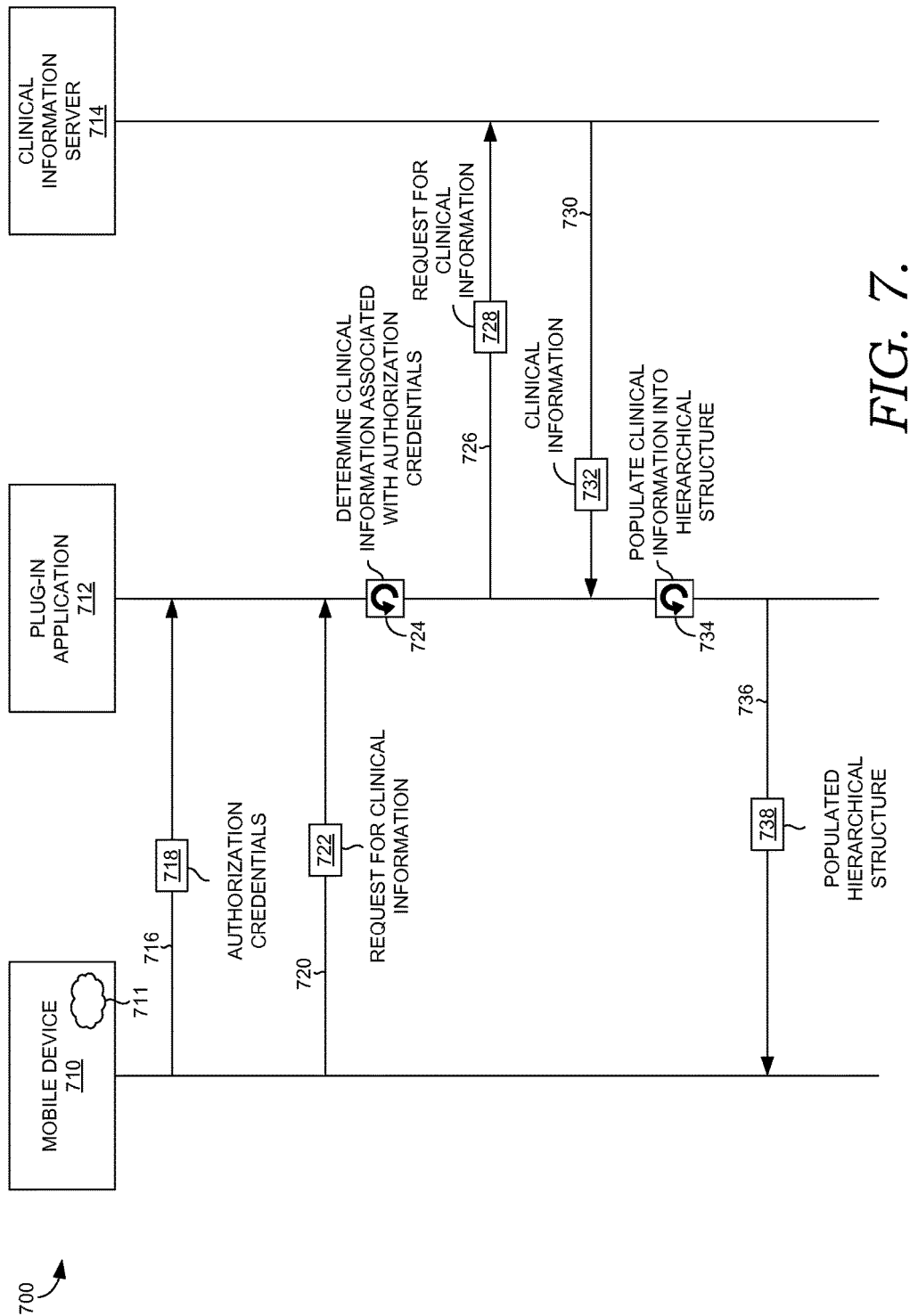
FIG. 7 depicts an illustrative process-flow diagram that depicts a method of accessing clinical information on a mobile device according to an embodiment of the present invention.

In one embodiment, the present invention is directed toward a clinical plug-in application on a mobile device that retrieves clinical information. The clinical information is communicated to a clinical framework application on the mobile device where it is subsequently rendered for display. FIG. 7 is a process-flow diagram, referenced generally by the numeral 700, that illustrates a method to perform this process. FIG. 7 depicts a mobile device 710 with a framework application 711, a plug-in application 712, and a clinical information service 714.

The mobile device 710 may be any type of wireless-telecommunications device. Such devices may include fixed, mobile, and portable devices including cellular telephones, personal digital assistants, tablet personal computers (tablet PCs), and devices that are built into automobiles, televisions, computers, and the like. The mobile device 710 may include global positioning system (GPS) technology. Further, the mobile device 710 includes a set of native controls. These native controls are well-known in the art and may include drop-down lists, spinners, free text, slide bars, flicks, pinch and stretch, drag, and the like.

The framework application 711, which is native to the operating system of the mobile device 710, enables the mobile device 710 to receive clinical information from the plug-in application 712 and render the clinical information for display to the user. As well, the framework application 711 enables the user of the mobile device 710 to input one or more values that are used by the plug-in application 712 to create a clinical order. The plug-in application 712 communicates with the framework application 711 through an application programming interface (API).

The plug-in application 712 is created by a third-party solution team and, as mentioned, communicates with the framework application 711 on the mobile device 710 through the API. The combination of a native framework application and an API enables third-party solution teams to build standard plug-in applications that work with a variety of operating systems on different types of mobile devices. This, in turn, reduces production time for the solution teams. The plug-in application 712 also communicates with one or more of the clinical information servers 714 to retrieve requested clinical information or to communicate clinical orders. The mobile device 710, the framework application 711, and the plug-in application 712 may correspond to the mobile device 210, the framework application 211, and the plug-in application 216 of FIG. 2. These components also correspond to the components discussed above with respect to FIGS. 3-4.

The clinical information server 714 comprises one or more servers affiliated with a healthcare facility. For example, the clinical information server 714 may be an electronic medical record associated with the healthcare facility. The electronic medical record may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

The clinical information server 714 may also include a real-time location (RTLS) service that tracks the location of patients and clinicians through the use of, for example, radio-frequency identification (RFID) tags. Additionally, the clinical information server 714 may include a scheduling/staffing server that tracks scheduling and staffing data for the healthcare facility, or an order server that receives clinical orders and, for example, stores the clinical order in association with a patient in the electronic medical record. All of the servers mentioned above may communicate with each other to return the requested clinical information to the plug-in application 712 as explained more fully below.

At step 716, the plug-in application 712 receives a set of authorization credentials 718 from the mobile device 710. The set of authorization credentials 718 are associated with a user role and/or a user identity. For example, the set of authorization credentials 718 may be associated with Nurse Ratchett, or the set of authorization credentials 718 may be associated with the clinical role nurse shift manager. The set of authorization credentials 718 may include, for example, personnel IDs stored in an authorization service affiliated with a healthcare facility (such as, for example, the authorization service 214 of FIG. 2). The set of authorization credentials 718 are only received by the plug-in application 712 if the user of the mobile device 710 has been authenticated.

At step 720, the plug-in application 712 also receives a request 722 for clinical information from the mobile device 710. The request 722 may be received simultaneously with the set of authorization credentials 718. The request 722 received by the plug-in application 712 is specific for that particular plug-in application 712. In other words, the plug-in application 712 is created to retrieve a certain set of clinical information and will only respond to requests to retrieve that set of clinical information. The set of clinical information may include, for example: IV pump locations that are located close to the user, scheduling or staffing information, patient lists, patients that are located close to the user, clinical ordering information, or other types of clinical information that are relevant to the user.

At step 724, the plug-in application 712 determines what type of clinical information is available to the user based on the set of authorization credentials 718. For example, suppose that the plug-in application 712 is designed to retrieve a set of clinical information comprising a patient list. The set of clinical information can also include information such as patient location, lab results, procedure results, consult notes, and the like. Based on the set of authorization credentials 718, the plug-in application 712 may only retrieve and return a small subset of this clinical information. By way of illustrative example, suppose the set of authorization credentials 718 indicates that the user requesting the patient list is a respiratory therapist. Based on the set of authorization credentials 718, the plug-in application 712 only returns a patient list with location information. On the other hand, suppose the set of authorization credentials 718 indicates that the user is a physician caring for the patients on the patient list. In this case, based on the set of authorization credentials 718, the plug-in application 712 returns the patient list with all of the accompanying information (location, lab results, procedure results, consult notes, etc.).

At step 726, the plug-in application 712 communicates a request 728 for clinical information to the clinical information server 714. The request 728 is only for clinical information that is associated with the set of authorization credentials 718. Further, the plug-in application may send the request 728 to multiple clinical information servers 714 in order to retrieve all of the requested clinical information.

In one aspect, the request 728 may be for a portion of clinical information. For example, a set of clinical information may have already been displayed to the user, but the user is requesting some additional information. The plug-in application may make a request for the portion of clinical information to supplement the already displayed clinical information. At step 730, the clinical information 732 is received from the clinical information server 714. Next, at step 734, the clinical information 732 is parsed and populated into a generic hierarchical structure based upon a classification scheme.

In general, the generic hierarchical structure is structured according to a classification scheme which includes, at its broadest level, one or more meta-types. A meta-type may be, among other things, a person, place, or thing. Every piece of clinical information that is populated into the generic hierarchical structure is classified under one of the meta-types. For example, patients on a patient list would be classified under a person meta-type, while IV pumps would be classified under a thing meta-type. Meta-types allow the user to better understand how data is being organized. Although three meta-types have been mentioned, it is contemplated that additional meta-types may be added depending on the type of clinical information being received.

Under a meta-type, clinical information can be further organized according to items and categories. An item is a discrete piece of clinical information such as an individual patient, an individual location such as a cafeteria, or an individual piece of equipment such as an IV pump. Each item is associated with a meta-type (i.e., patient with person meta-type, cafeteria with place meta-type, and intravenous pump with thing meta-type). A collection of items is classified as a category. The items and categories may be nested. An exemplary populated generic hierarchical structure is shown below:

Person (meta-type)
    Clinicians (category)
        Nurses (category)
            ICU Nurses (category)
                Mary Gannon (item)
                Stephanie Rogers (item)
        Physicians (category)
            Bjarat Sutaryia (item)
    Patients in my Location (category)
        Bob Jones (item)
        Tom Fryer (item)

Figure 12:
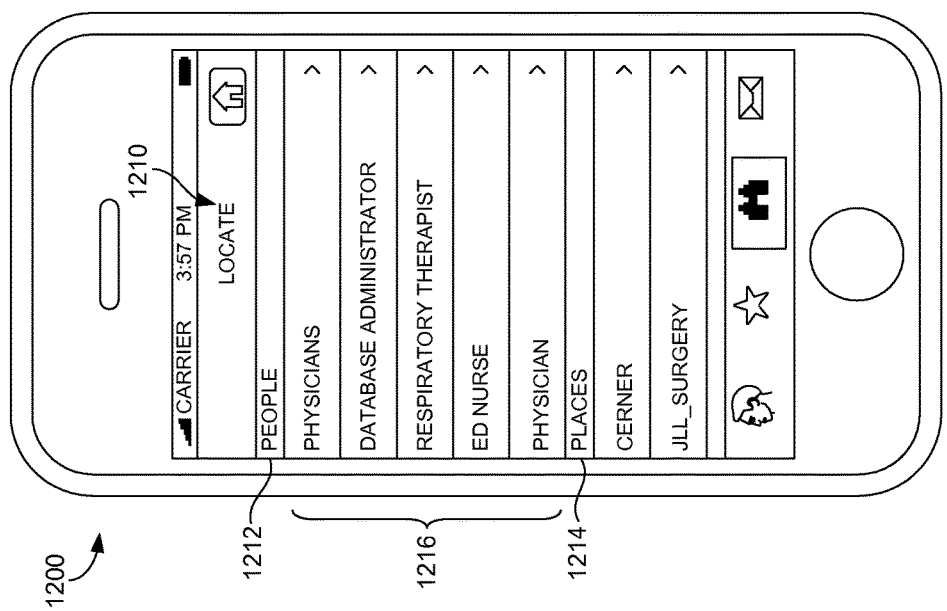
FIG. 12 depicts an exemplary user interface illustrating a mobile device displaying a clinical information according to an embodiment of the present invention.

FIG. 12 depicts an exemplary user interface 1200 illustrating how clinical information is organized and displayed on a mobile device using the hierarchical structure discussed above. The user interface 1200 comprises a heading 1210 that indicates what type of clinical information is being displayed. In this case, it is location information. The user interface 1200 also comprises two meta-types—people 1212 and places 1214. All of the clinical information will be categorized under these two meta-types. Additionally, the user interface 1200 depicts categories 1216.

Figure 13:
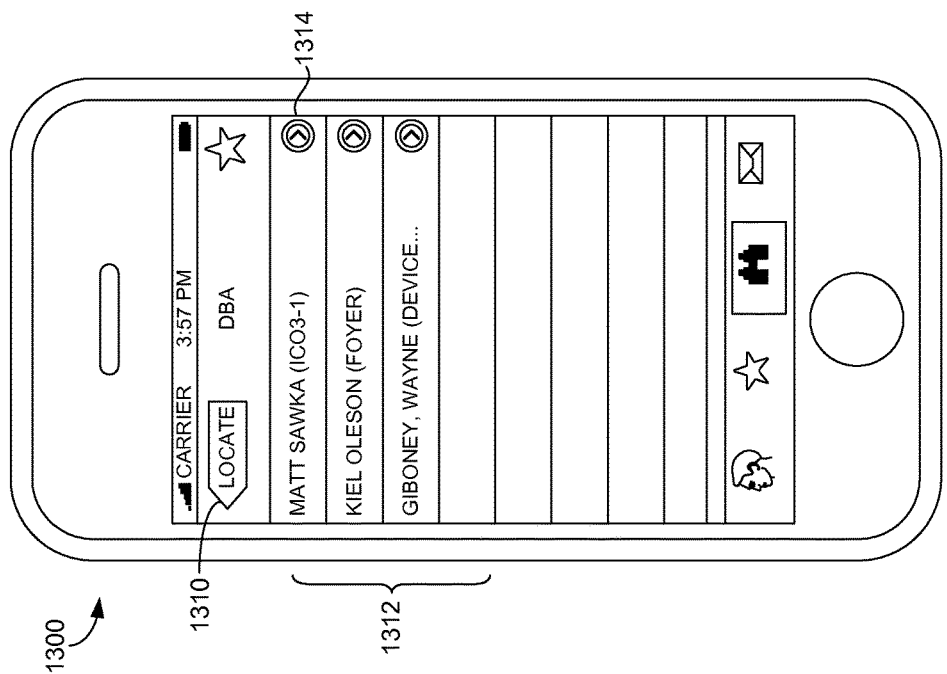
FIG. 13 depicts an exemplary user interface illustrating a mobile device displaying a detail view of clinical information according to an embodiment of the present invention.

Turning now to FIG. 13, an exemplary user interface 1300 is depicted that illustrates the clinical information that is presented once a user selects, for example, one of the categories 1216 of FIG. 12. The user interface 1300 comprises a heading 1310 that corresponds to the heading 1210 of FIG. 12. The heading 1310 is selectable and enables the user to navigate back to a home screen such as that depicted in the user interface 1200. The user interface 1300 also comprises one or more items 1312 related to one of the categories selected by the user (for example, one of the categories 1216 of user interface 1200). The items 1312 include selectable arrows 1314 that enable the user to navigate to additional information regarding the items 1312.

Turning back to FIG. 7, each item of the clinical information 732 received by the plug-in application 712 may include additional information that may be displayed in association with the item, or may be displayed upon the user selecting an option to display the additional information. For example, each item of the clinical information 732 may be associated with additional information such as an item priority which indicates a level of importance of the item. A high priority item may be displayed, for example, in red or have a red flag associated with the item. The item priority may be used to alert the user to an event such as, for example, indicating that a blood pressure value is elevated by displaying the blood pressure value in association with a red flag.

Additional information may also include an item attribute. The item attribute is used to notify the user of a state of an item. For example, a new lab result could be displayed with an asterisk to indicate that the item is new. Or, in another example, a follow-up item may also be displayed with a visual indicator to indicate its follow-up state. Additional information may also include a title which is the primary name of an item. For example, for the patient Tom Jones, the title would be "Tom Jones."

Still further, additional information for an item may include a subtitle which indicates a secondary piece of information about the item. This could be, for example, a location of the patient (for example, "second floor—East"). Additional information may include an item information which is a tertiary piece of information about the item such as, for example, a blood pressure value. Additionally, information may include another piece of information about the item which is known as an item detail information. This could be, for example, a respiratory rate.

The plug-in application 712 is able to specify generic rendering instructions for the clinical information 732. The rendering instructions are used by the mobile device 710 to render the clinical information 732 for display to the user. For example, the rendering instructions may specify a layout of the clinical information 732 on the display screen of the mobile device 710.

Figure 8:
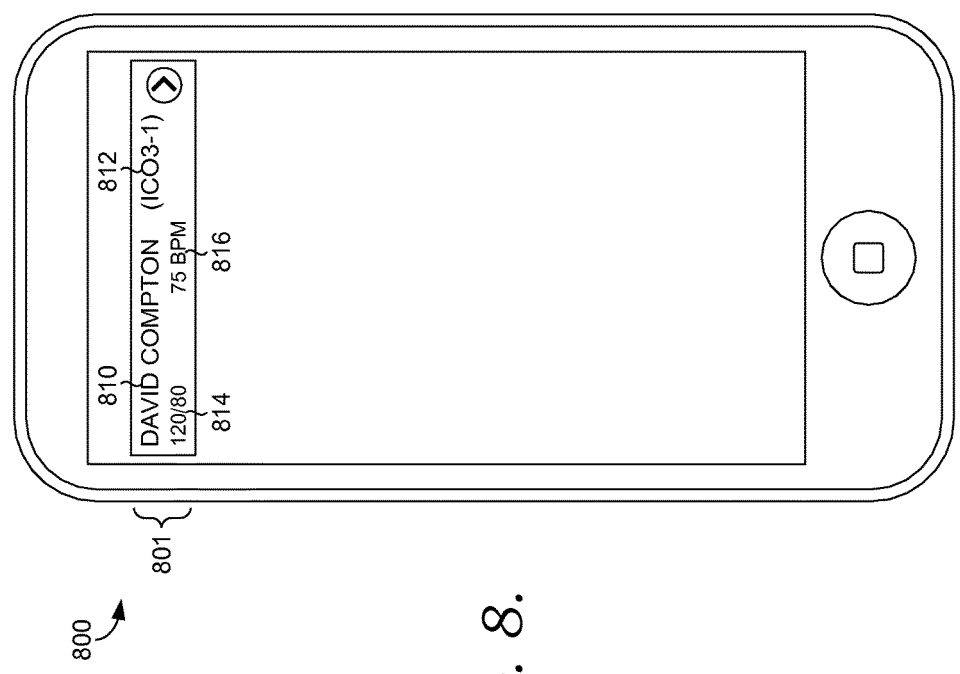
FIG. 8 depicts an exemplary display of an item of clinical information according to an embodiment of the present invention.

FIG. 8 depicts an exemplary user interface 800 illustrating an item 801 of clinical information, including additional information. The item 801 may be displayed on a mobile device such as the mobile device 710 of FIG. 7. The item 801 includes a title 810 which indicates the name of a patient, as well as a subtitle 812 which indicates a location of the patient. Further, the item 801 includes an item information 814 which, in this case, is a blood pressure value, and the item 801 also includes a detail information 816 which is a respiratory rate. The layout of these pieces of information is determined by the rendering instructions generated by a plug-in application. As mentioned above, the additional information associated with an item may be displayed upon a user selecting the item. For example, when a user selects the arrow 1314 of FIG. 13, the user may be directed to a display comprising the item in association with the additional information.

Returning to FIG. 7, still further, each item of clinical information 732 may be associated with a uniform resource locator (URL) that directs the user to a Web page when the item is selected. The Web page provides even more information about the item. In one aspect, the Web page may be a static Web page. In another aspect, the Web page may be a dynamic Web page. The plug-in application 712 may specify a refresh rate for the item, and the Web page may be reloaded based on the specified refresh rate. All of these pieces of additional information about an item, alone or in combination with each other, may be displayed in association with the item of clinical information 732.

Figure 14:
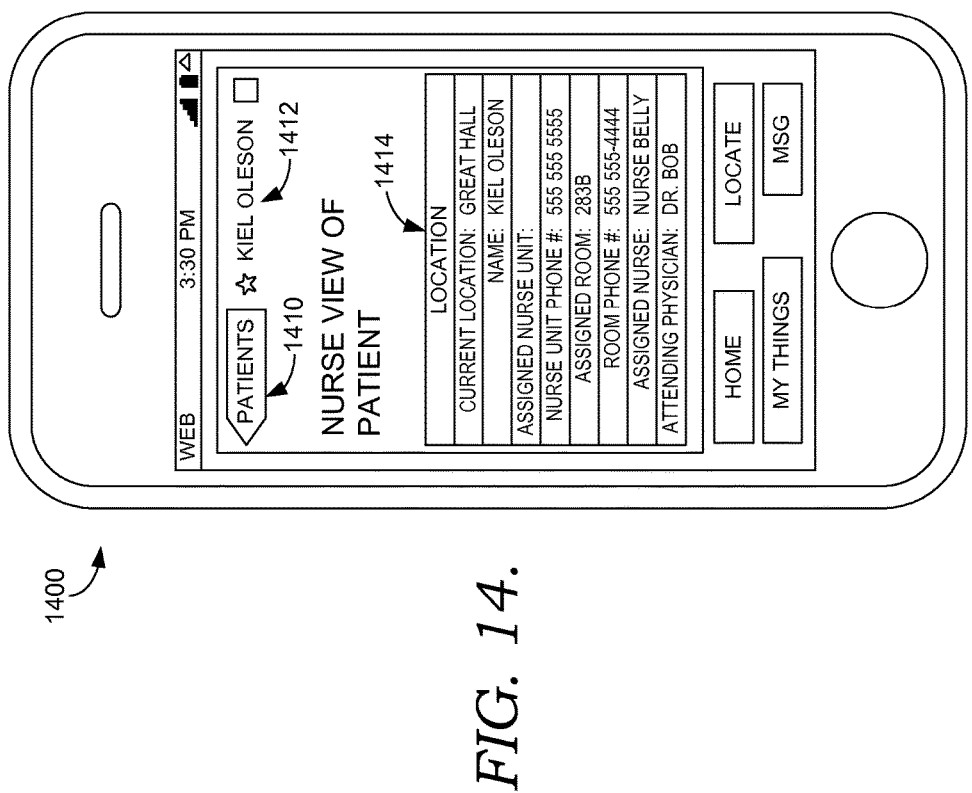
FIG. 14 depicts an exemplary user interface illustrating a mobile device displaying a Web page associated with a clinical patient according to an embodiment of the present invention.

FIG. 14 depicts an exemplary user interface 1400 of a mobile device. The user interface 1400 depicts a Web page 1414 that is presented to the user when the user selects an item. The user interface 1400 comprises a selectable heading 1410 that identifies what type of clinical information is being presented. The user interface 1400 also includes another heading indicating an item 1412 (in this case, patient Kiel Oleson) of which more information is sought. Thus, upon the user selecting the item 1412 on a previous user interface (such as, for example, the user interface 1300 of FIG. 13), a URL associated with the item 1412 directs the user to the Web page 1414. As mentioned above, the Web page 1414 may be a static Web page or a dynamic Web page. The Web page 1414 provides additional information about the item 1412.

Turning back to FIG. 7, after the clinical information 732 is populated into the generic hierarchical structure, the populated hierarchical structure 738 is communicated to the mobile device 710 where it is subsequently rendered for display to the user. The display may include, for example, the user interfaces 1200, 1300, and 1400 of FIGS. 12-14. As mentioned above, several populated hierarchical structure from different plug-in applications may be communicated to the mobile device 710. The mobile device 710 combines the disparate hierarchical structures into a master hierarchical structure that contains all of the requested clinical information. The master hierarchical structure is subsequently rendered for display.

Figure 9:
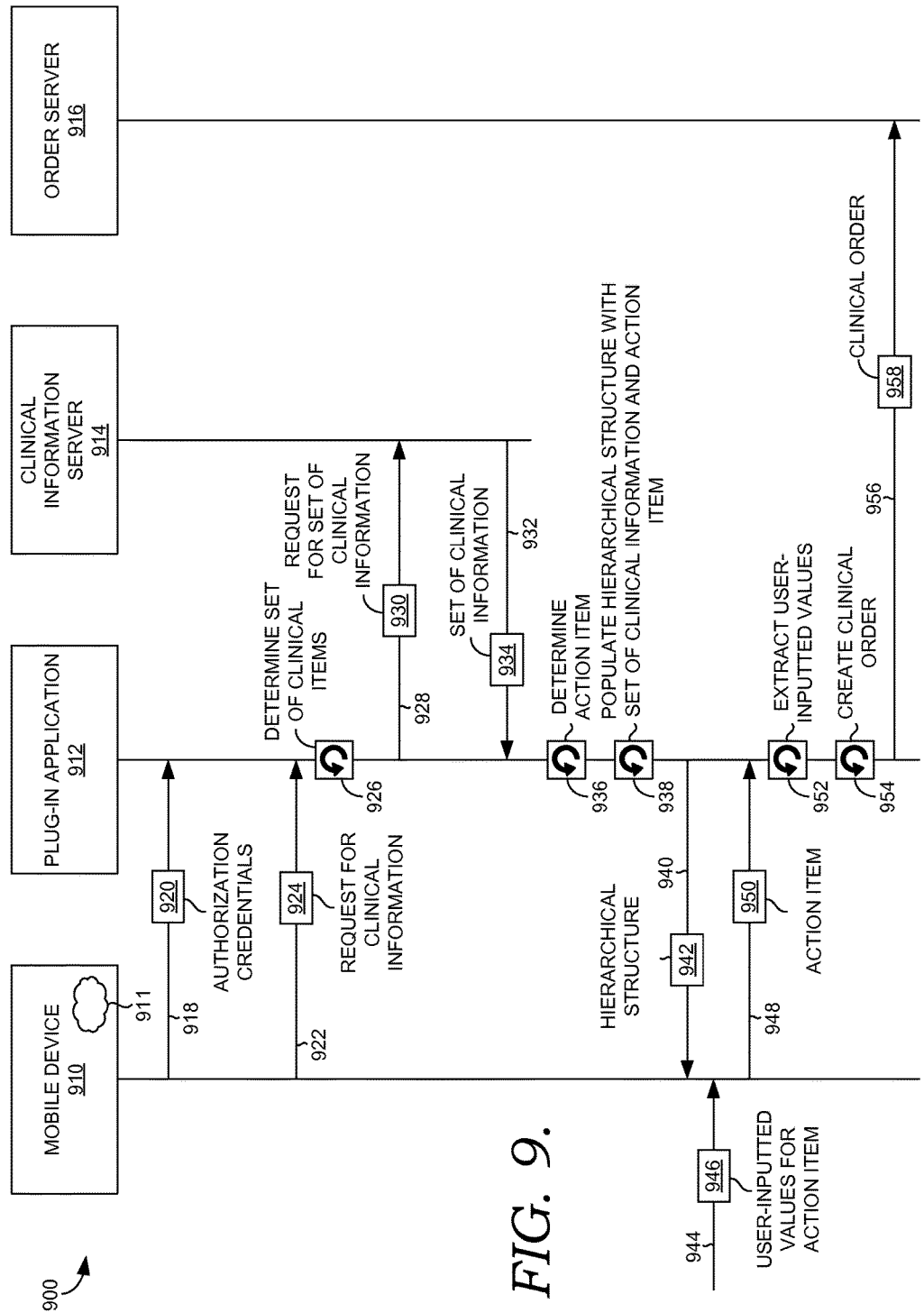
FIG. 9 depicts an illustrative process-flow diagram that depicts a method of utilizing a plug-in application to create a clinical order on a mobile device according to an embodiment of the present invention.

Turning now to FIG. 9, a process-flow diagram, referenced generally by the numeral 900, illustrates a method of generating a clinical order on a mobile device using a plug-in application in combination with a framework application on the mobile device. FIG. 9 depicts a mobile device 910, a framework application 911, a plug-in application 912, a clinical information server 914, and an order server 916.

The mobile device 910, the framework application 911, the plug-in application 912, and the clinical information server 914 may correspond to the mobile device 710, the framework application 711, the plug-in application 712, and the clinical information server 714 of FIG. 7, and, as such, will not be discussed in detail herein. The order server 916 comprises a server that is configured to receive clinical orders. A clinical order may be, for example, an order related to a patient such as an order for a certain medication, an order that the patient be associated with a certain medical device, an order for a procedure, and the like. After receiving a clinical order, the order server 916 may, for example, update a patient's electronic medical record to reflect the clinical order and notify one or more clinicians of the pending clinical order. The order server 916 may be the same as the clinical information server 914.

At step 918, the mobile device 910 communicates a set of authorization credentials 920 to the plug-in application 912. As well, at step 922, the mobile device 910 communicates a request 924 for clinical information to the plug-in application 912. The request 924 may be a request for patient information from a clinician caring for the patient. The request 924 may also be a request to place a clinical order for the patient. At step 926, the plug-in application determines a set of clinical information available to the user based on the set of authorization credentials 920 as outlined above with respect to FIG. 7. At step 928, the plug-in application 912 communicates a request 930 for the set of clinical information to the clinical information server 914, and, at step 932, the set of clinical information 934 is received by the plug-in application 912.

At step 936, the plug-in application 912 determines an action item for at least one item of the clinical information 934. The action item is associated with the item of the clinical information 934 and is actuated when the user selects the item of clinical information 934. The action item may comprise several different pieces of information. The action item may include an action item URL that includes a URL with a set of placeholders. The action item URL ultimately enables the user to place a clinical order. This process will be explained in greater depth below. The action item may also comprise an action display. The action display specifies rendering instructions used by the mobile device 910 to render a display screen that displays a clinical order and the appropriate input fields needed to complete the clinical order. Additionally, the action item may comprise an action behavior type which specifies generic actions that correspond to native controls on the mobile device 910.

At step 938, the set of clinical information 934, including the determined action item, is parsed and populated into a generic hierarchical structure, and, at step 940, the hierarchical structure 942 is communicated to the mobile device 910 where it is subsequently rendered for display. Upon the user selecting the at least one item of the clinical information 934 associated with the action item, the user is directed to a display screen that enables the user to input values. The mobile device 910 replaces the action item URL placeholders with the user-inputted values, and, at step 948, the mobile device 910 communicates the action item URL 950 to the plug-in application 912. The action item URL 950 comprises the original action item URL, but, instead of placeholders, the action item URL has one or more user-inputted values. For example, an exemplary action item URL 950 that is usable for associating a patient with a medical device might be, "https://localhost:8080/assignPatientToDevice?patient=123&device=234."

At step 952, the plug-in application 912 extracts the user-inputted values from the action item URL 950. Further, at step 954, the plug-in application 912 creates a clinical order using the user-inputted values, and, at step 956, the clinical order 958 is communicated to the order server 916.

In one aspect of the invention, the plug-in application 912 may customize one or more action item URLs for a particular clinician. For example, based on the authorization credentials 920 received at step 918, the plug-in application 912 may identify the clinician as having one or more customized action item URLs that enable the clinician to place a clinical order that is outside the scope of normal clinical orders.

Figure 10:
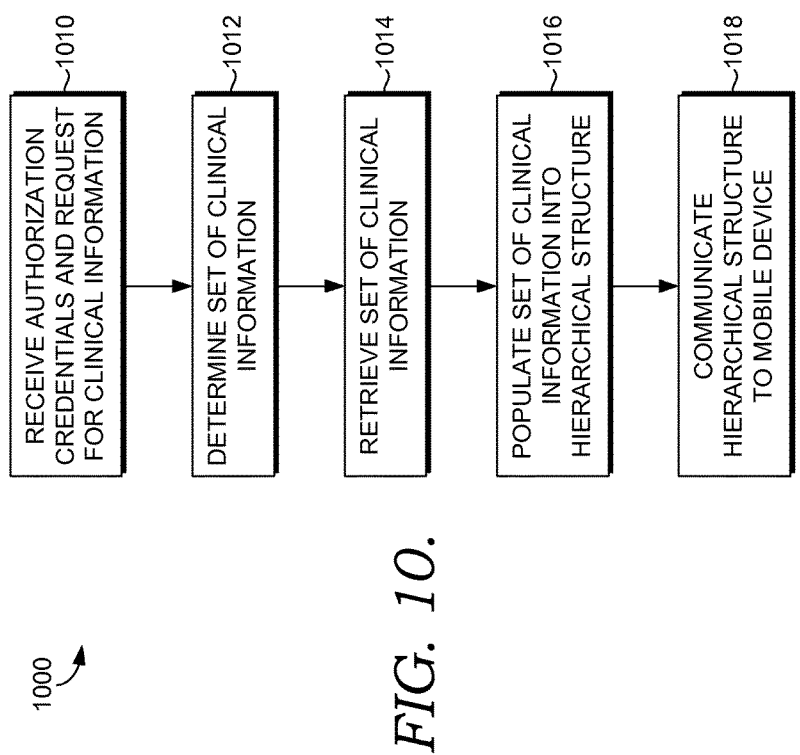
FIG. 10 depicts a flow diagram illustrating a method of using a plug-in application on a mobile device to retrieve clinical information according to an embodiment of the present invention.

FIG. 10 depicts a flow diagram illustrating a method 1000 of utilizing a plug-in application on a mobile device to retrieve clinical information. At step 1010, the plug-in application receives from the mobile device a set of authorization credentials along with a request for clinical information. The set of authorization credentials is received subsequent to the mobile device exchanging a token string that is associated with the user or a user role for the set of authorization credentials.

At step 1012, the plug-in application determines a set of clinical information based on the authorization credentials. For example, one set of authorization credentials may allow full access to a set of clinical information, while another set of authorization credentials may allow access to a small subset of clinical information. At step 1014, the plug-in application retrieves the determined set of clinical information from one or more clinical information servers. One portion of the set of clinical information may be retrieved from one clinical information server while another portion of clinical information is retrieved from another clinical information server. Further, at step 1016, the set of clinical information is parsed and populated into a generic hierarchical structure according to a classification scheme as outlined above with respect to FIG. 7. The hierarchical structure is subsequently communicated to the mobile device at step 1018 where it is rendered for display to the user.

Figure 11:
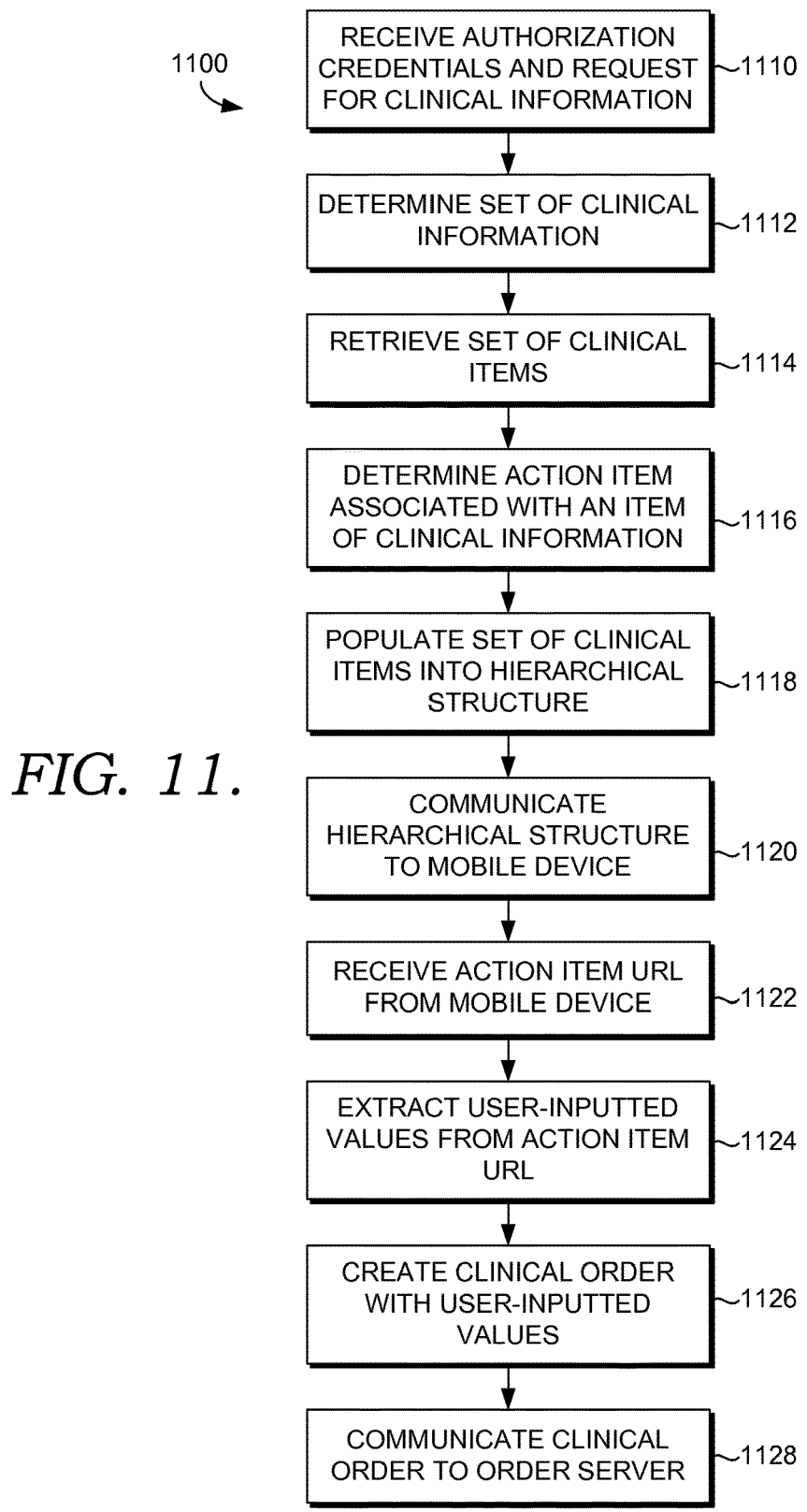
FIG. 11 depicts a flow diagram illustrating a method of using a plug-in application on a mobile device to enable a clinician to place a clinical order using the mobile device according to an embodiment of the present invention.

FIG. 11 depicts a flow diagram illustrating a method 1100 of using a plug-in application on a mobile device to enable a clinician to place a clinical order using the mobile device. At step 1110, the plug-in application receives a set of authorization credentials along with a request for clinical information. The set of authorization credentials and the request for clinical information are received from a framework application residing on the mobile device, for example, the framework application 911 and the mobile device 910 of FIG. 9. The request for clinical information includes a request to place a clinical order.

At step 1112, the plug-in application determines a set of clinical information associated with the set of authorization credentials. If the set of authorization credentials received at step 1110 indicates that the user does not have the authority to place a clinical order, a notification may be sent to the user informing the user of this information. At step 1114, the set of clinical information is retrieved from one or more clinical information servers. The set of clinical information includes one or more items of clinical information.

At step 1116, the plug-in application determines that at least one of the items of clinical information is associated with an action item. The action item enables the user to take some type of action with respect to the item of clinical information such as placing a clinical order. The action item includes an action item URL with a set of placeholders. At step 1118, the set of clinical information including the item of clinical information associated with the action item is parsed and populated into a generic hierarchical structure.

At step 1120, the populated hierarchical structure is communicated to the framework application residing on the mobile device. Once the hierarchical structure has been communicated to the mobile device, the mobile device renders the hierarchical structure for display to the user. When the user selects the item of clinical information associated with the action item URL, the user is directed to a user interface that enables the user to input a series of values corresponding to the clinical order using the native controls of the mobile device. The mobile device subsequently replaces the placeholders with the user-inputted values.

At step 1122, the mobile device communicates the action item URL to the plug-in application, and the plug-in application receives the action item URL. The action item URL now comprises the URL with a set of user-inputted values in place of the placeholders. At step 1124, the plug-in application extracts the user-inputted values from the action item URL, and, at step 1126, the plug-in application creates a clinical order with the user-inputted values. At step 1128, the clinical order is communicated to one or more order servers.

In conclusion, the clinical plug-in application interacts with a framework application on a mobile device to receive requests for clinical information, retrieve the clinical information from one or more clinical information servers, and communicate the clinical information to the mobile device where it is subsequently rendered for display to the user. Additionally, the clinical plug-in application interacts with the framework application to enable a user to place a clinical order using the native controls of the mobile device.

Figure 15:
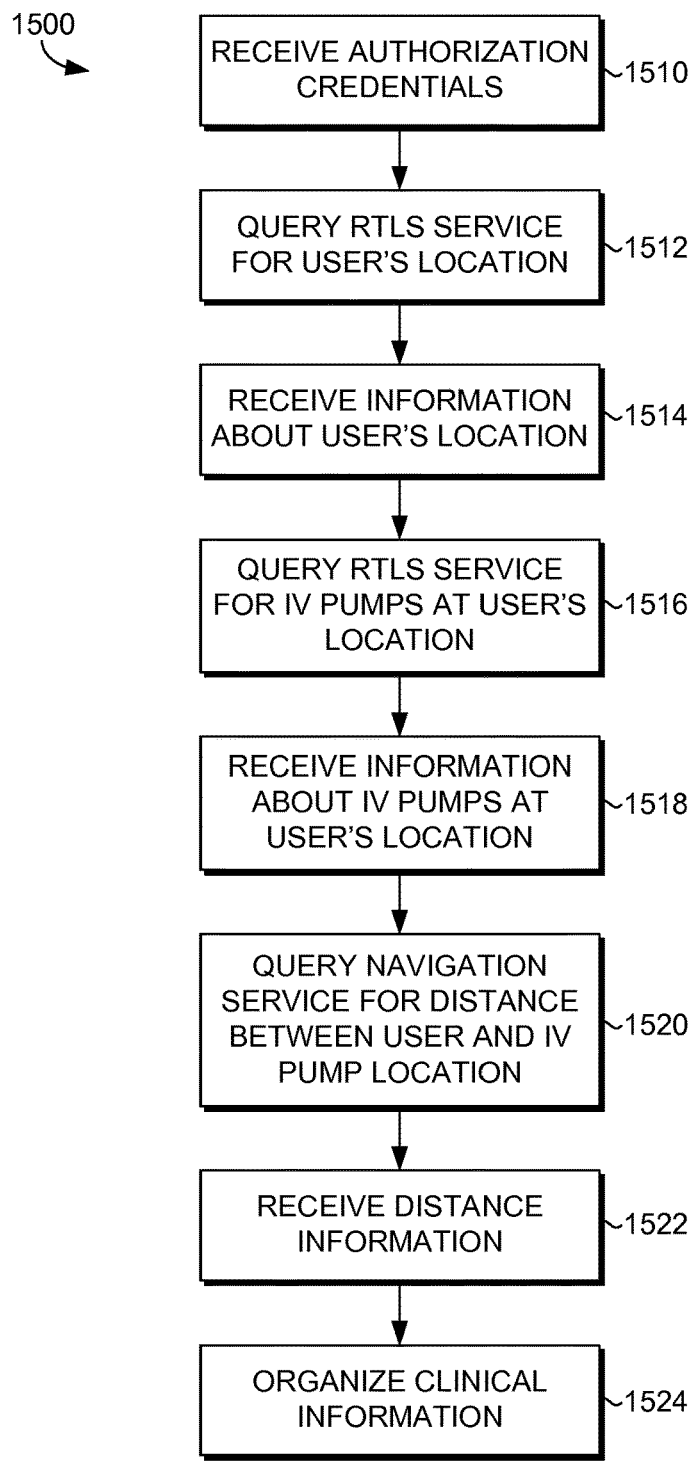
FIG. 15 depicts a flow diagram illustrating a method of accessing clinical information about intravenous pump locations that are located close to a user according to an embodiment of the present invention.

Several examples will now be provided to better illustrate the claimed invention. FIG. 15 depicts a flow diagram illustrating a method 1500 of providing clinical information regarding IV pump locations that are located close to a user using a plug-in application. The plug-in application is designed by a third-party solution team to specifically retrieve this type of information. At step 1510, the plug-in application receives a set of authorization credentials associated with the user or user role. At step 1512, the plug-in application queries a real time location service (RTLS) for the user's location. The RTLS service utilizes RFID tags to track and locate not only clinicians, but patients and equipment as well. At step 1514, the plug-in application receives information about the user's location from the RTLS service. As an alternative to the above, the plug-in application may obtain user location information using a GPS system present on the user's mobile device.

At step 1516, the plug-in application queries the RTLS service to obtain location information about IV pumps that are located close to the user's location. At step 1518, the plug-in application receives information about IV pumps that are located close to the user's location. Continuing, at step 1520, a navigation service is queried for information concerning the distance between the user's location and the IV pump locations, and, at step 1522, the plug-in application receives this information from the navigation service. As can be seen, the plug-in application may make any number of requests for clinical information from any number of clinical information servers. At step 1524, the plug-in application organizes the clinical information into a generic hierarchical structure. Further, the clinical information may be ordered for display based on, for example, which IV pump is located closest to the user.

Figure 16:
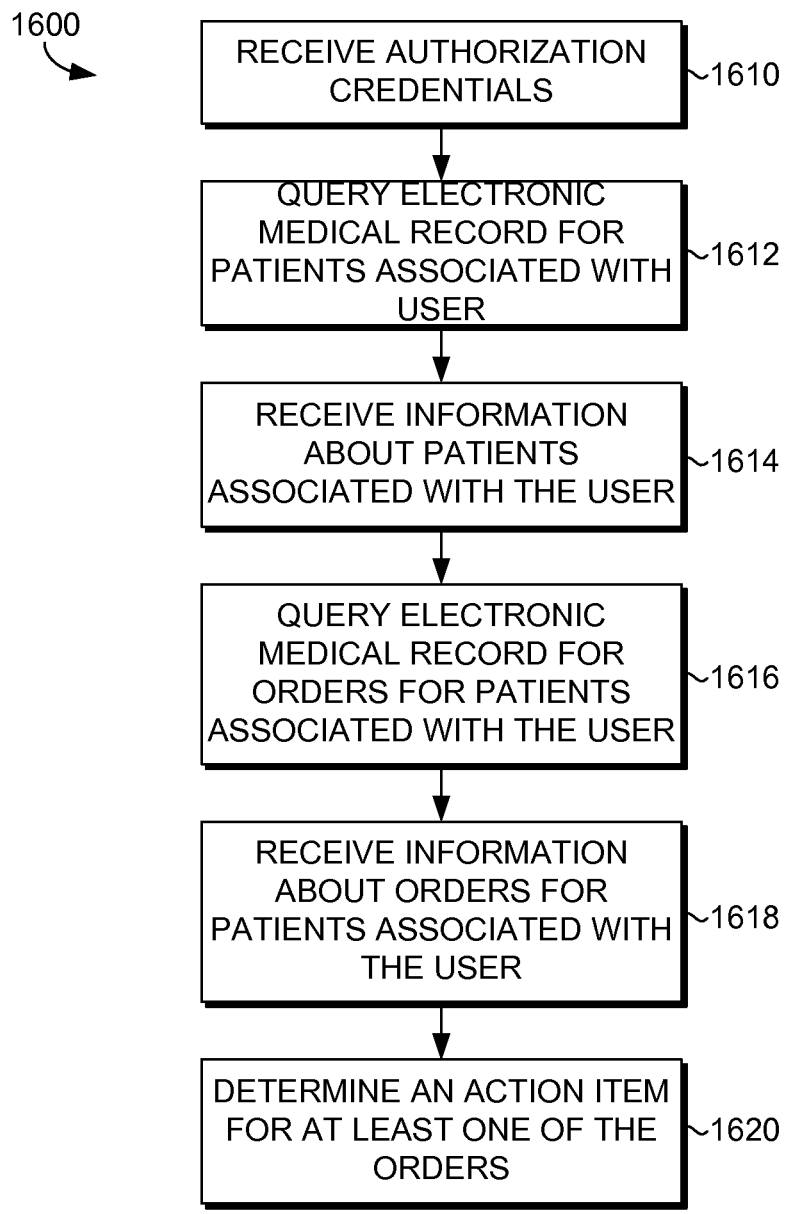
FIG. 16 depicts a flow diagram illustrating a method of accessing clinical information about clinical orders associated with a patient according to an embodiment of the present invention.

FIG. 16 depicts a flow diagram illustrating a method 1600 of providing clinical information regarding current clinical orders for patients associated with a user utilizing a plug-in application. At step 1610, the plug-in application receives authorization credentials associated with the user or a user role; the authorization credentials may include a personnel ID. At step 1612, the plug-in application queries an electronic medical record for a list of patients associated with the user. And, at step 1614, this information is received from the electronic medical record. At step 1616, the plug-in application again queries the electronic medical record to determine whether any clinical orders exist for patients on the patient list. Again, at step 1618, this information is received from the electronic medical record. At step 1620, the plug-in application determines an action item for at least one of the clinical orders. The action item enables the user to place a clinical order using the native controls of the mobile device as outlined above with respect to FIG. 11.

Figure 17:
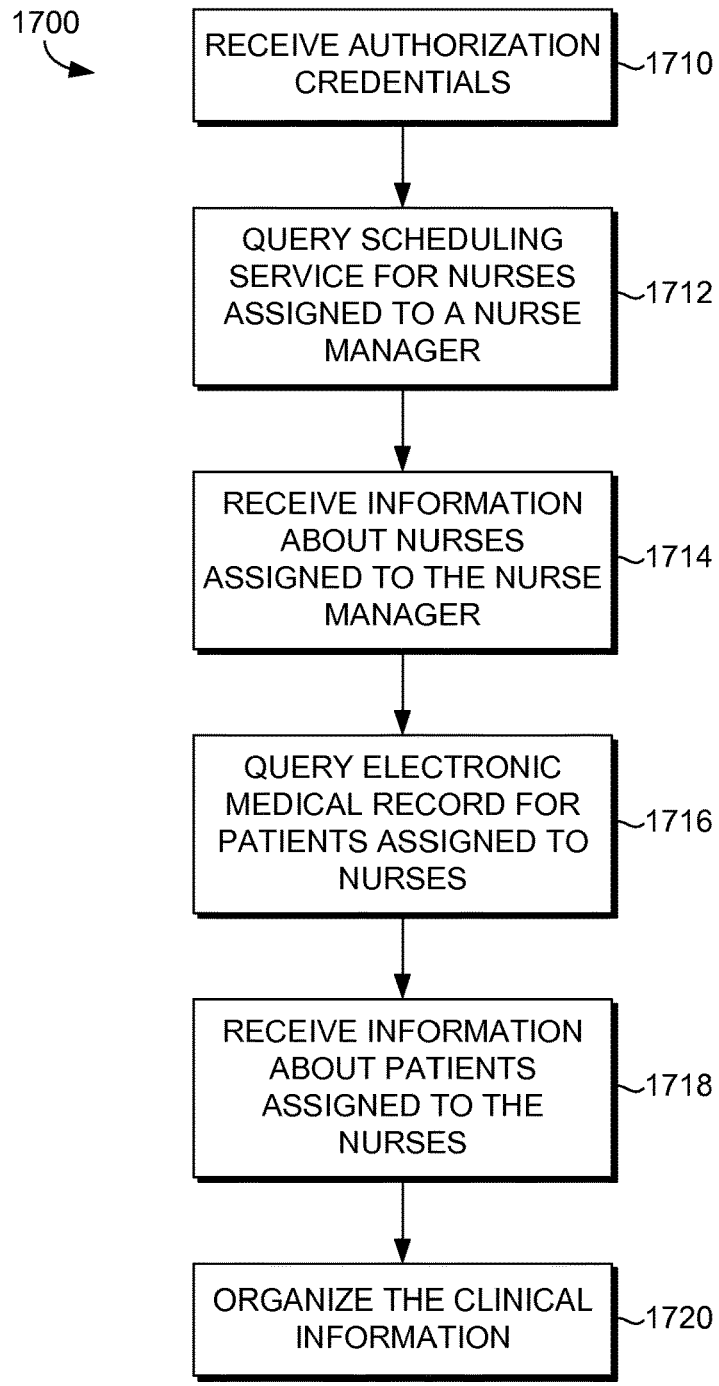
FIG. 17 depicts a flow diagram illustrating a method of accessing clinical information regarding nurses associated with a nurse manager according to an embodiment of the present invention.

FIG. 17 depicts a flow diagram illustrating a method 1700 of providing clinical information regarding which nurses are assigned to work under a nurse shift manager, and which patients are assigned to those nurses. The clinical information is provided by a plug-in application. At step 1710, authorization credentials are received by the plug-in application. The authorization credentials are associated with a user role such as a nurse shift manager. At step 1712, the plug-in application queries a scheduling service to determine which nurses are assigned to the nurse shift manager. At step 1714, information about which nurses are assigned to the nurse shift manager is returned to the plug-in application.

At step 1716, an electronic medical record is queried to obtain information regarding which patients are assigned to the nurses, and, at step 1718, this information is received by the plug-in application. At step 1720, the plug-in application parses the clinical information and populates the clinical information into a generic hierarchical structure. The information is structured according to meta-types, categories, and items. For example, "Nurse A" may be a category, and the patients assigned to Nurse A may be items nested into that category.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer-storage media having computer-executable instructions embodied thereon that, when executed by a plug-in application on a remote mobile device, facilitate a method for generating an interactive user interface displayed on a display screen of the mobile device, the interactive user interface being usable for accessing clinical information on the remote mobile device by a user of the remote mobile device, the method comprising:
    at the plug-in application on the remote mobile device:
        simultaneously receiving from a framework application built into an operating system of the remote mobile device: (1) a set of authorization credentials associated with the user of the remote mobile device, and (2) a request for clinical information from the user of the remote mobile device;
        determining a set of clinical information associated with the set of authorization credentials associated with the user of the remote mobile device;
        retrieving the set of clinical information from a clinical information server;
        parsing and populating the set of clinical information into a generic hierarchical structure based on a predetermined classification scheme according to the set of authorization credentials associated with the user of the remote mobile device, wherein the set of clinical information includes one or more action items, wherein at least a first action item is in the form of a uniform resource locator (URL) with a set of placeholders for receiving extractable user-inputted values associated with the first action item, wherein at least a second action item is an action display that specifies rendering instructions used by the remote mobile device to render the interactive user interface displayed on the display screen of the remote mobile device, and wherein at least a third action item is an action behavior type that specifies generic actions that correspond to native controls on the remote mobile device; and
        communicating the populated generic hierarchical structure to the framework application built into the operating system of the remote mobile device where it is displayed to the user on the interactive user interface according to the rendering instructions specified by the action display.

2. The media of claim 1, wherein the set of authorization credentials are associated with a clinical role or a clinical identity.

3. The media of claim 1, wherein the set of clinical information comprises intravenous pump locations that are close to the user.

4. The media of claim 1, wherein the set of clinical information comprises scheduling information associated with one or more clinicians at a healthcare facility.

5. The media of claim 1, wherein the generic hierarchical structure is organized according to the following classification scheme:
    (1) meta-type, wherein a meta-type is a person, place, or thing,
    (2) item, wherein an item is an individual item associated with a meta-type, and
    (3) category, wherein a category is a collection of items.

6. The media of claim 5, wherein each item comprises the following item information:
    (1) item priority, wherein an item priority is used to indicate a level of importance of the item,
    (2) item attribute, wherein an item attribute is used to indicate a state of the item,
    (3) title, wherein a title is the primary name of the item,
    (4) subtitle, wherein a subtitle includes a secondary piece of information about the item,
    (5) item information, wherein an item information includes a tertiary piece of information about the item, and
    (6) detail information, wherein a detail information is an additional piece of information about the item.

7. The media of claim 5, wherein each item is associated with the one or more action items or one or more uniform resource locators (URLs) for one or more Web pages.

8. The media of claim 7, wherein the one or more Web pages comprise either a static Web page or a dynamic Web page.

9. The media of claim 1, wherein the at least one action item in the form of the URL with the set of place holders is useable to generate a clinical order on the remote mobile device.

10. One or more non-transitory computer-storage media having computer-executable instructions embodied thereon that, when executed by a plug-in application on a remote mobile device, facilitate a method for generating a user interface for display on a display screen of the mobile device, the user interface being usable for creating a clinical order on the remote mobile device, the method comprising:
    at the plug-in application on the remote mobile device:
        receiving from a framework application built into the operating system of the remote mobile device: (1) a set of authorization credentials associated with a clinician, and (2) a request for clinical information;
        determining a set of clinical information associated with the set of authorization credentials associated with the clinician and the request for clinical information;
        retrieving the set of clinical information from a clinical information server, the set of clinical information including at least one item of clinical information;
        generating at least one action item for the at least one item of clinical information that is customized for the clinician, the at least one action item comprising a first action item uniform resource locator (URL) with a set of placeholders for receiving one or more extractable clinician-inputted values associated with the at least one action item;

populating a generic hierarchical structure with the set of clinical information including the at least one action item based on a predetermined classification scheme;

communicating the populated generic hierarchical structure to the framework application that is built into the operating system of the remote mobile device where it is displayed to the clinician via the user interface rendered on the display screen of the remote mobile device, wherein the user interface rendered on the display screen of the remote mobile device comprises one or more input fields for receiving one or more clinician-inputted values associated with the set of clinical information, and wherein the mobile device receives the one or more clinician-inputted values associated with the set of clinical information from the clinician, and wherein the framework application that is built into the operating system of the remote mobile device replaces the set of placeholders in the first action item URL with the one or more clinician-inputted values to generate a second action item URL;

incident to communicating the populated generic hierarchical structure to the framework application that is built into the operating system of the remote mobile device, receiving the second action item URL from the framework application that is built into the operating system of the remote mobile device;

extracting the one or more clinician-inputted values from the second action item URL;

creating a clinical order based on the one or more clinician-inputted values extracted from the second action item URL; and communicating the clinical order to one or more order servers.

11. One or more non-transitory computer-storage media having computer-executable instructions embodied thereon that, when executed by a plug-in application on a remote mobile device, facilitate a method for generating a user interface rendered on a display screen of the mobile device, the user interface being usable for accessing clinical information on the remote mobile device, the method comprising:

at the plug-in application on the remote mobile device:

receiving from a framework application built into the operating system of the remote mobile device a request for clinical information;

receiving from the framework application built into the operating system of the remote mobile device a set of authorization credentials associated with a clinician, wherein the clinician initiated the request for clinical information via the user interface rendered on the display screen of the remote mobile device;

determining a set of clinical information associated with the set of authorization credentials, the set of clinical information comprising information about one or more clinical patients;

retrieving the set of clinical information associated with the set of authorization credentials from a clinical information server;

parsing and populating the set of clinical information associated with the set of authorization credentials into a generic hierarchical structure based on a predetermined classification scheme, the predetermined classification scheme comprising: 1) a meta-type section comprising one of a person, place, or thing, 2) an item section comprising one or more items associated with the meta-type, and 3) a category section comprising one or more categories, each category comprising a collection of items of the one or more items, wherein the one or more items include one or more action items, wherein at least one action item in the one or more action items is in the form of a uniform resource locator (URL) with a set of placeholders for receiving one or more extractable clinician-inputted values associated with the at least one action item; and communicating the populated generic hierarchical structure to the framework application built into the operating system of the remote mobile device for display to the clinician via the user interface rendered on the display screen of the remote mobile device, wherein the user interface rendered on the display screen of the remote mobile device comprises one or more input fields for receiving the one or more clinician-inputted values associated with the set of clinical information.

12. The media of claim 11, wherein the set of clinical information associated with the set of authorization credentials comprises a list of clinical patients that are being cared for by the clinician.

13. The media of claim 9, wherein the at least one action item in the form of the URL with the set of place holders is useable to generate the clinical order on the remote mobile device by receiving, from the framework application built into the operating system of the remote mobile device, the uniform resource locator (URL) with the set of placeholders replaced by the one or more clinician-inputted values.

* * * * *